US008285086B2

(12) United States Patent
Nishikawa et al.

(10) Patent No.: US 8,285,086 B2
(45) Date of Patent: Oct. 9, 2012

(54) OPTICAL FIBER SENSOR

(75) Inventors: Satoshi Nishikawa, Tokyo (JP);
Masakazu Takabayashi, Tokyo (JP);
Kiichi Yoshiara, Tokyo (JP); Eiji Yagyu, Tokyo (JP); Tateki Mitani, Tokyo (JP);
Yutaro Hamatani, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 342 days.

(21) Appl. No.: 12/529,865

(22) PCT Filed: Jan. 7, 2008

(86) PCT No.: PCT/JP2008/050029
§ 371 (c)(1),
(2), (4) Date: Sep. 3, 2009

(87) PCT Pub. No.: WO2008/111320
PCT Pub. Date: Sep. 18, 2008

(65) Prior Publication Data
US 2010/0080502 A1    Apr. 1, 2010

(30) Foreign Application Priority Data

Mar. 9, 2007 (JP) ................................. 2007-059311
Mar. 9, 2007 (JP) ................................. 2007-059312

(51) Int. Cl.
*G02B 6/00* (2006.01)
*G02B 6/34* (2006.01)
(52) U.S. Cl. ......................................... 385/12; 385/37
(58) Field of Classification Search ........................ None
See application file for complete search history.

(56) References Cited

U.S. PATENT DOCUMENTS

| 6,069,985 | A | * | 5/2000 | Albin et al. | 385/12 |
| 7,184,135 | B2 | | 2/2007 | Laffont et al. | |
| 2006/0013527 | A1 | * | 1/2006 | Morel et al. | 385/24 |
| 2008/0069497 | A1 | * | 3/2008 | Tissot et al. | 385/37 |

FOREIGN PATENT DOCUMENTS

| JP | 2003-195097 | 7/2003 |
| WO | 02 44697 | 6/2002 |

(Continued)

OTHER PUBLICATIONS

Chen, Xianfeng et al., "Optical Chemsensor Based on Etched Tilted Bragg Grating Structures in Multimode Fiber", IEEE Photonics Technology Letters, vol. 17, No. 4, pp. 864-866, (Apr. 2005).

(Continued)

*Primary Examiner* — Hemang Sanghavi
(74) *Attorney, Agent, or Firm* — Oblon, Spivak, McClelland, Maier & Neustadt, L.L.P.

(57) ABSTRACT

An optical fiber sensor measuring refractive index of a medium with high sensitivity in a wide range. The optical fiber sensor includes an optical fiber causing a transmission loss due to leakage in the clad propagation mode from a portion of a core and a clad where a Bragg grating is provided, a light source permitting light in a wavelength band in the clad propagation mode to enter the optical fiber, and a light-receiving section receiving the transmitted or reflected light transmitted through the core and the clad at the portion where the Bragg grating is provided. The refractive index of the medium to be measured in contact with the clad is measured according to total intensity of the light received by the light-receiving section. The Bragg grating is inclined at a predetermined angle of inclination to the vertical line vertical to the length direction of the optical fiber.

3 Claims, 21 Drawing Sheets

FOREIGN PATENT DOCUMENTS

| WO | WO 2004/036280 A1 | 4/2004 |
|---|---|---|
| WO | 2006 126468 | 11/2006 |

OTHER PUBLICATIONS

Zhao, Chun-Liu et al., "Simultaneous Temperature and Refractive Index Measurements Using a 3° Slanted Multimode Fiber Bragg Grating", Journal of Lightwave Technology, vol. 24, No. 2, pp. 879-883, (Feb. 2006).

Office Action issued Aug. 30, 2011 in Japan Application No. 2009-503913 (With Partial English Translation).

U.S. Appl. No. 12/745,815, filed Jun. 2, 2010, Nishikawa, et al.

* cited by examiner

FIG. 2
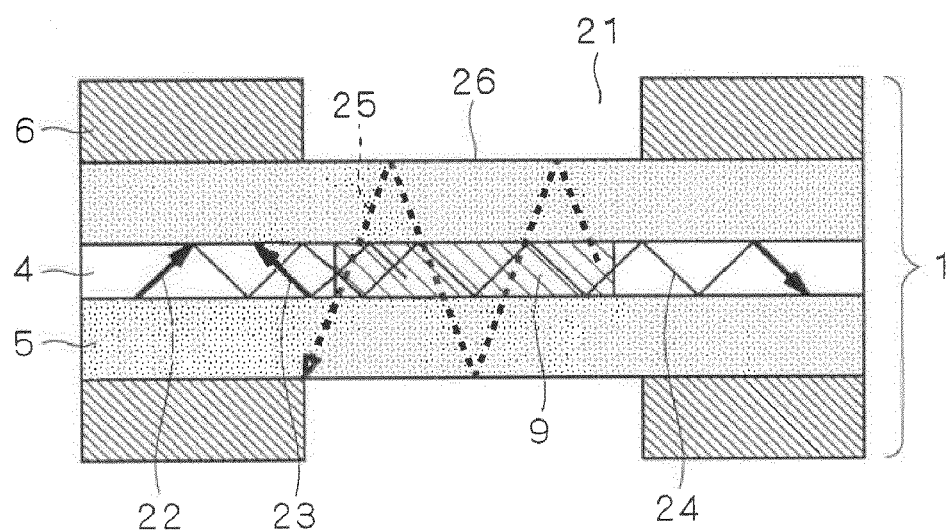
(a)
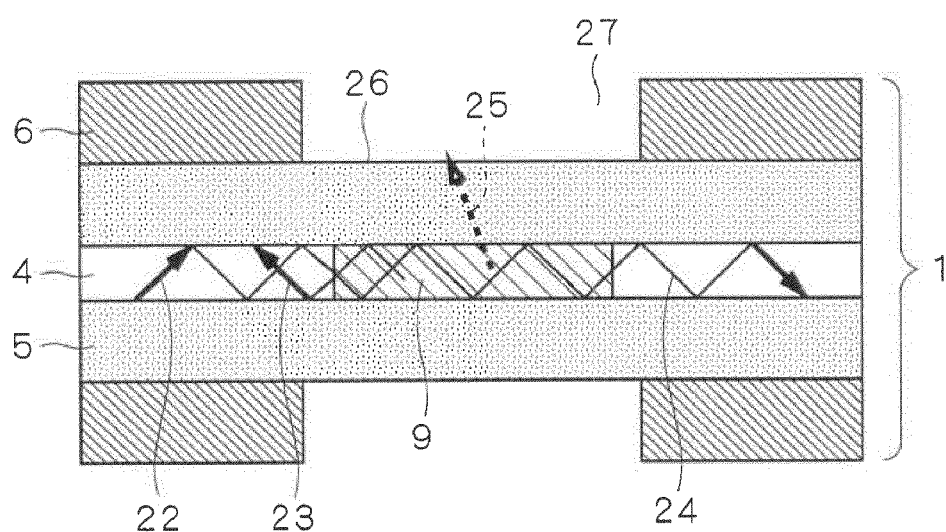
(b)

F I G . 7
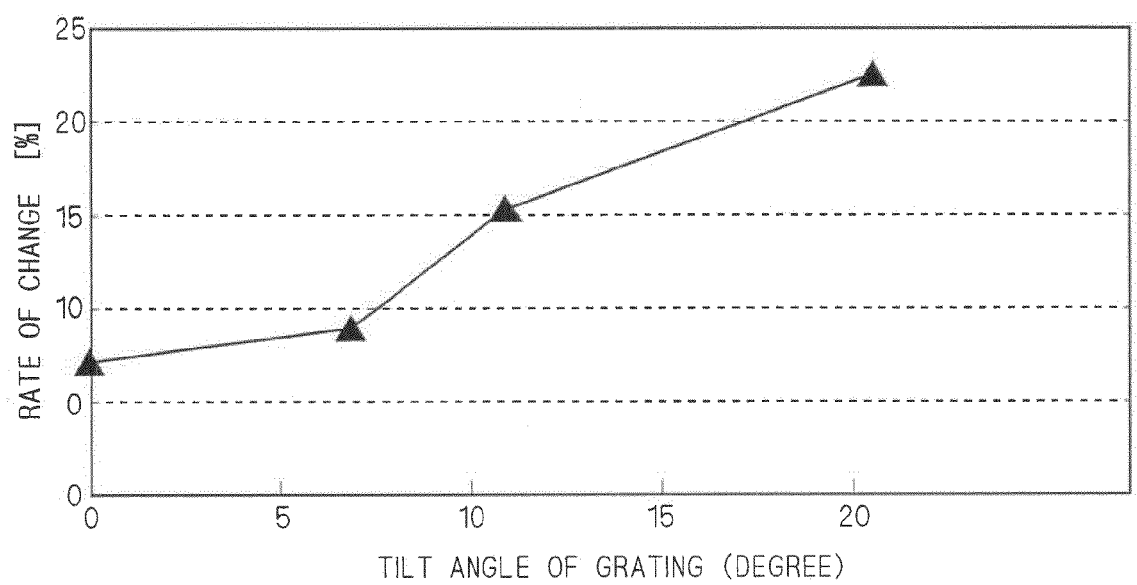

FIG. 8
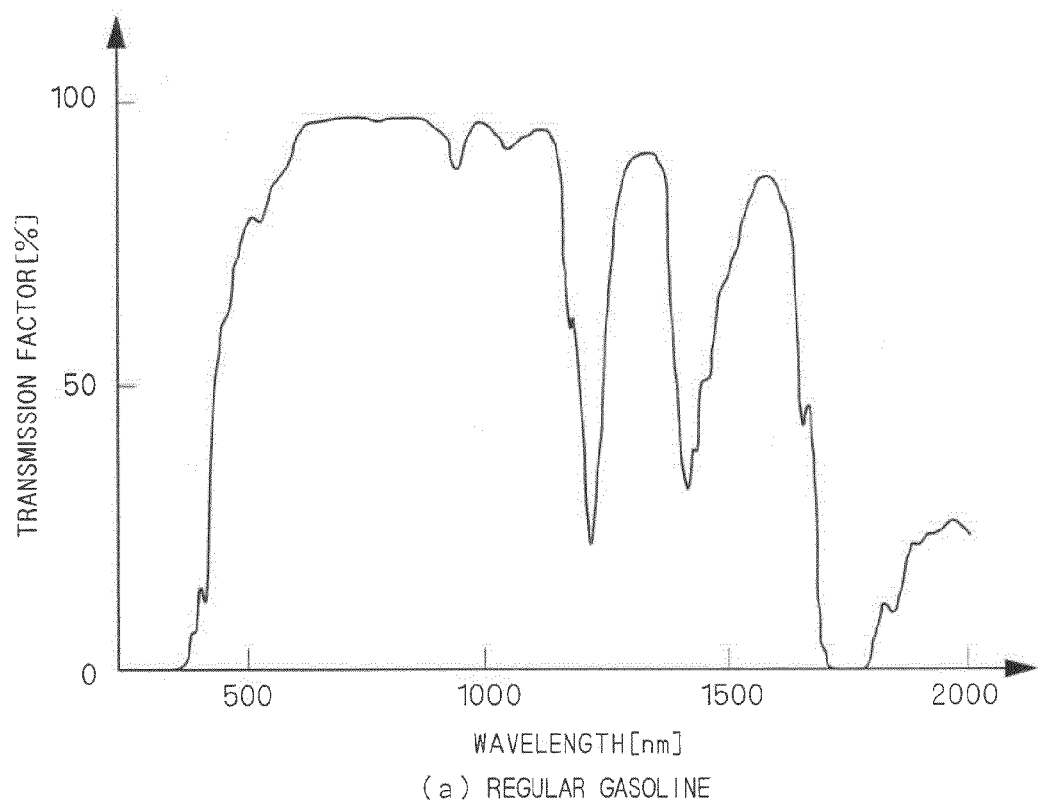
(a) REGULAR GASOLINE
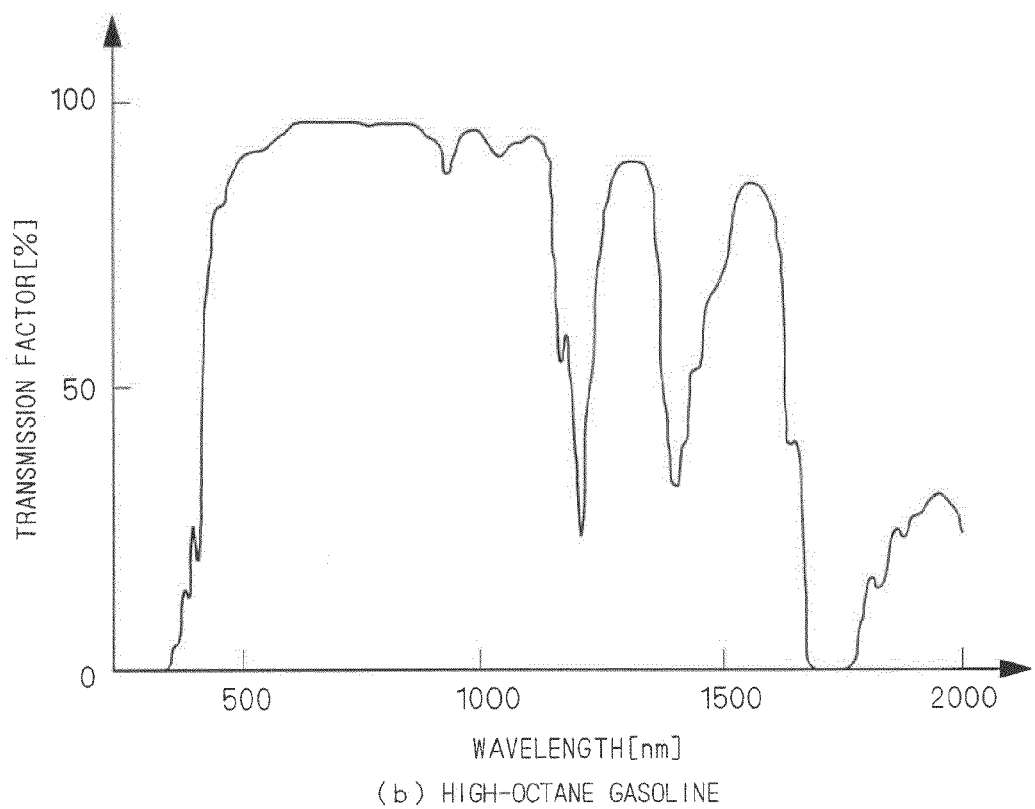
(b) HIGH-OCTANE GASOLINE

F I G . 1 3
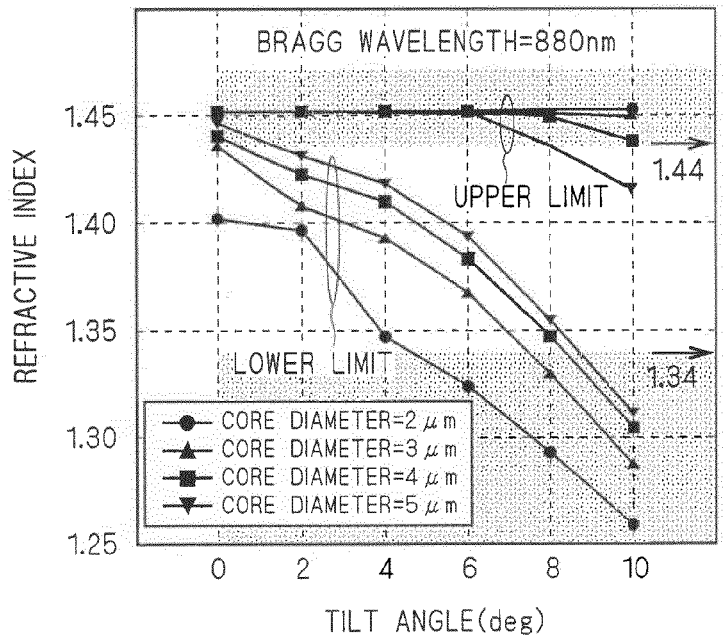
F I G . 1 4
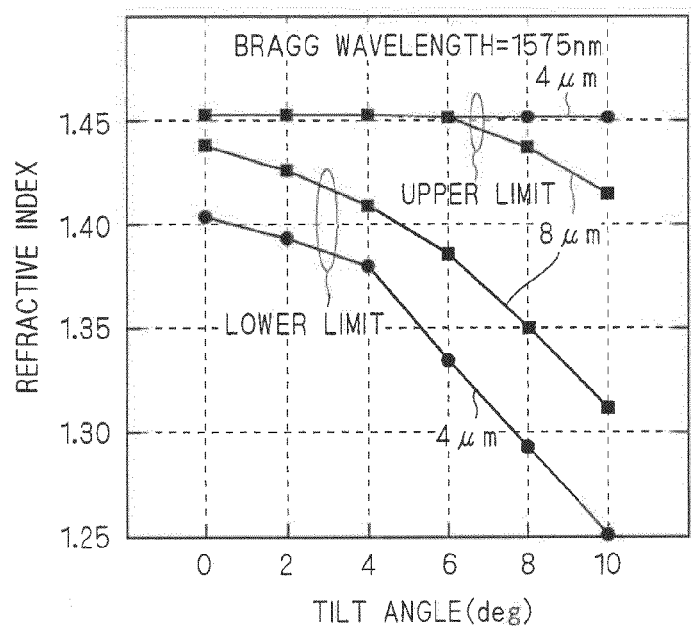

F I G . 1 5
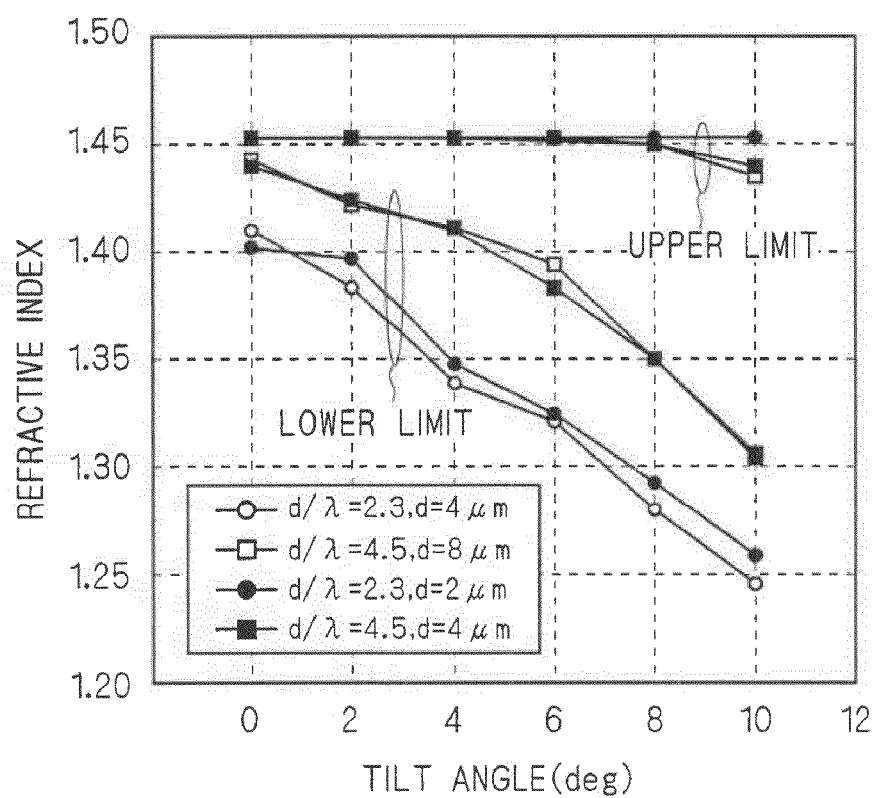

F I G . 2 4
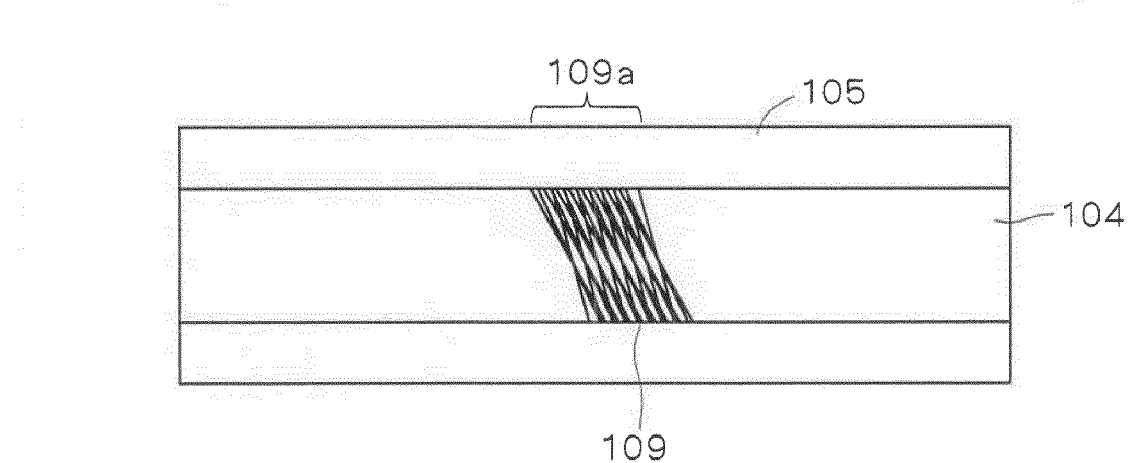

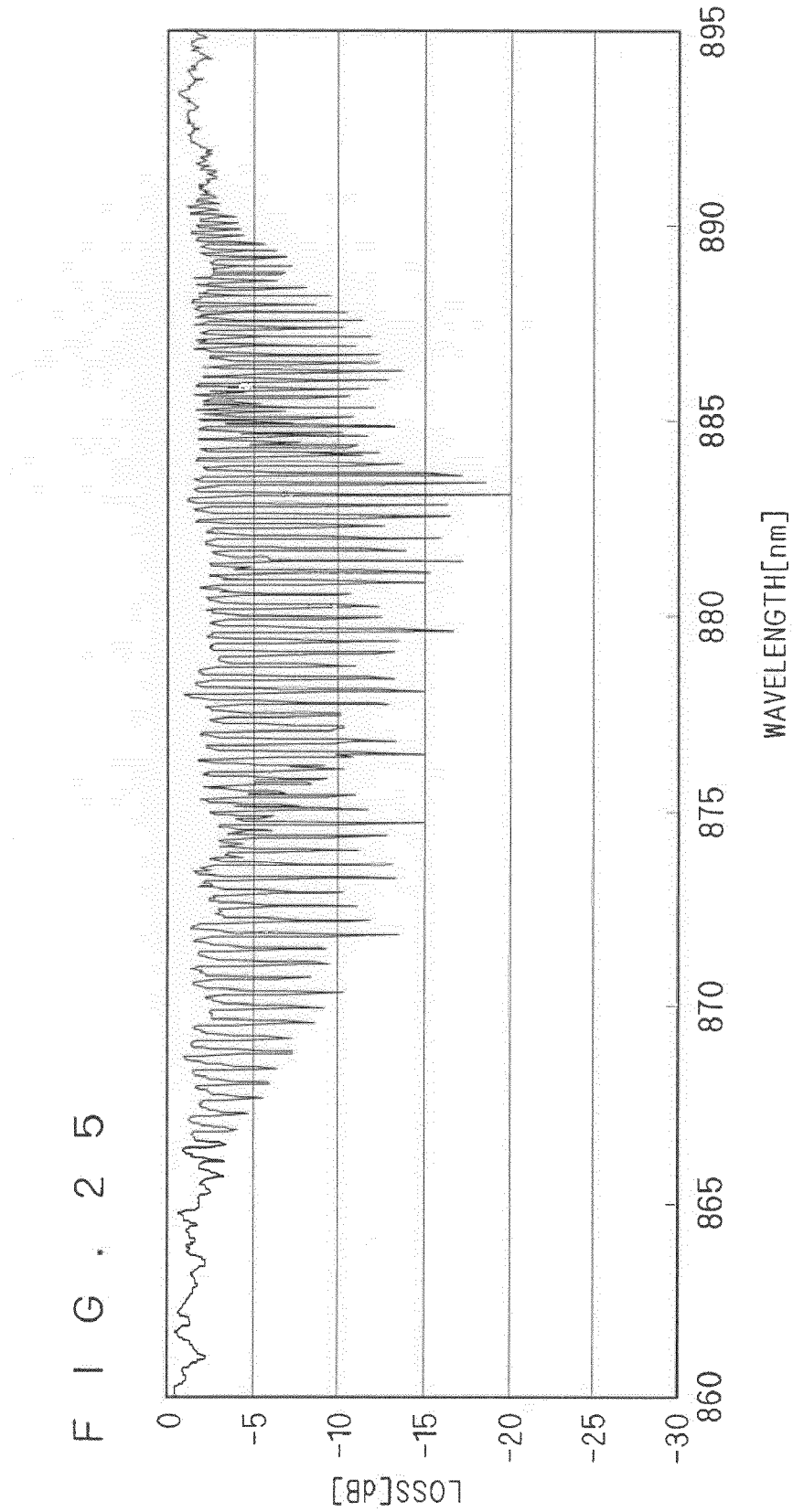

OPTICAL FIBER SENSOR

TECHNICAL FIELD

The present invention relates to an optical fiber sensor, and more particularly to an optical fiber sensor capable of detecting liquid properties by utilizing a refractive index.

BACKGROUND ART

Pure gasoline used as fuel for motorcar engines includes light gasoline whose main ingredient is a hydrocarbon such as heptane, pentane and the like, heavy gasoline whose main ingredient is a hydrocarbon such as benzene and the like and medium gasoline (normal regular gasoline) which is a medium type of these two. If the heavy gasoline is used as fuel for an engine whose ignition timing and the like are controlled to be matched to the light gasoline, for example, ignition of the engine is delayed. Further, in this engine, there arises deterioration in cold startability and deterioration in driving performance, such as a breathing phenomenon and the like, and there causes an increase of toxic components in exhaust fumes due to incomplete combustion.

In the United States, European countries and the like, alcohol-blended gasoline becomes widespread as fuel for automobiles in order to reduce the amount of oil consumed. If this alcohol-blended fuel is used for an engine which is matched to the air fuel ratio of gasoline, the air fuel ratio becomes lean because the theoretical air fuel ratio of alcohol is lower than that of gasoline, and so on. For this reason, if the alcohol-blended fuel is used for a motorcar engine, it is necessary to control an actuator such as a fuel injection valve or the like on the basis of detected alcohol content in the alcohol-blended fuel and adjust the air fuel ratio, the ignition timing and the like in accordance with the detected alcohol content rate.

Therefore, for motorcar engines, it is necessary to detect which type of gasoline is used, light, medium or heavy, and the alcohol content rate in the alcohol-blended fuel. It is further necessary to control the air fuel ratio, the ignition timing and the like in accordance with the detected value.

Whether the gasoline to be used is heavy or light is correlated with its refractive index. The refractive index of the heavy gasoline is large and that of light gasoline is small. Therefore, as a liquid property sensor for gasoline, a type of sensor to measure the change of the refractive index has been developed.

Patent Document 1 discloses a liquid property sensor which inputs light from a light source into a short-period tilted-grating and analyzes spectra of the output light by a signal analyzer. With a change in refractive index of a material surrounding the grating, a transmission spectra shape in a cladding propagation mode appearing in transmission factor properties changes. In Patent Document 1, by measuring the transmission spectrum and calculating a change in shape of an envelope, the refractive index of the surrounding of the grating is detected and the liquid properties are thereby detected.

Patent Document 2 discloses a liquid property sensor which inputs light from a light source into a short-period grating. Also in Patent Document 2, with a change in refractive index of a material surrounding the grating, the change in transmission spectra shape in the cladding propagation mode appearing in transmission factor properties is used. In Patent Document 2, by measuring a change in intensity of the output light due to the change in transmission spectra shape, the refractive index of the surrounding of the grating is detected.

Patent Document 1: International Publication No. 02/44697 brochure

Patent Document 2: International Publication No. 06/126468 Brochure

In the detection using the short-period tilted-grating, as disclosed in Patent Document 1, since it is necessary to measure the spectra shape of cladding propagation mode loss peak with high resolution of wavelength, an expensive measurement device such as a light spectrum analyzer or the like is needed. For this reason, in the liquid property sensor of Patent Document 1, it is difficult to measure the refractive index only with simple detection of the quantity of light.

Further in Patent Document 1, as the tilt angle of the grating increases, the lower limit of measurable range of refractive index can be enlarged toward the lower refractive index side but the upper limit accordingly decreases. As a result, Patent Document 1 has a problem of impairing the effect of enlarging the measurable range of refractive index.

On the other hand, in the detection using the short-period grating, as disclosed in Patent Document 2, since the change in spectra shape in the cladding propagation mode loss peak is detected with the change in the quantity of transmitted light, it is possible to measure the refractive index only with simple detection of the quantity of light. Patent Document 2, however, has a problem that the measurable range of refractive index can not be sufficiently enlarged.

DISCLOSURE OF INVENTION

The present invention is intended to solve the above problems, and it is an object of the present invention to provide an optical fiber sensor capable of measuring, a refractive index of a medium to be measured with high sensitivity in a wide refractive index range with a simple construction.

According to an aspect of the present invention, the optical fiber sensor includes an optical fiber including a core with a Bragg grating formed therein and a cladding, in which a transmission loss is caused by a leakage in a cladding propagation mode at a portion of the core and the cladding where the Bragg grating is formed, a light source for emitting light of the wavelength band in the cladding propagation mode into the optical fiber, and a light receiving part for receiving a transmitted light or a reflected light of the light passing through the core and the cladding at a position where the Bragg grating is formed, and detects a refractive index of a medium to be measured which is in contact with the cladding on the basis of the intensity of total light received by the light receiving part, and in the optical fiber sensor of the present invention, the Bragg grating has a predetermined tilt angle with respect to a vertical line in a longitudinal direction of the optical fiber.

In the above aspect of the present invention, since the Bragg grating has a predetermined tilt angle with respect to a vertical line in a longitudinal direction of the optical fiber, it is possible to measure a refractive index of a medium to be measured with high sensitivity in a wide refractive index range and with a simple construction.

According to another aspect of the present invention, the optical fiber sensor includes an optical fiber including a core with a Bragg grating formed therein and a cladding, in which a transmission loss is caused by a leakage in a cladding propagation mode at the cladding where the Bragg grating is formed, a light source for emitting light of the wavelength band in the cladding propagation mode into the optical fiber, and a light receiving part for receiving a transmitted light or a reflected light of the light passing through the cladding at a position where the Bragg grating is formed, and detects a refractive index of a medium to be measured which is in contact with the cladding on the basis of the intensity of total light received by the light receiving part, and in the optical fiber sensor of the present invention, the optical fiber is a multimode optical fiber and the Bragg grating has a tilt angle of 4.4° or more with respect to a vertical line in a longitudinal direction of the optical fiber.

In the another aspect of the present invention, since the optical fiber sensor includes the grating having a tilt angle of 4.4° or more, even if a multimode optical fiber is used as the optical fiber, it is possible to cause the cladding propagation mode and further possible to detect the refractive index of the medium to be measured which is in contact with the cladding at a region where the grating is formed. Further, since the optical fiber sensor in the present invention uses a multimode optical fiber, it is possible to enlarge the amount of change in the received light intensity with respect to the quantity of detected light and the refractive index change.

These and other objects, features, aspects and advantages of the present invention will become more apparent from the following detailed description of the present invention when taken in conjunction with the accompanying drawings.

BRIEF DESCRIPTION OF DRAWINGS

FIG. 2 is an illustration diagram showing a relation between a propagating light and a refractive index of liquid in the optical fiber sensor according to the first preferred embodiment of the present invention.

FIG. 7 is an illustration diagram showing a relation between the tilt angle and the rate of change in the optical fiber sensor according to the first preferred embodiment of the present invention.

FIG. 8 is a diagram showing changes of transmission factor according to wavelengths in regular gasoline and high-octane gasoline.

FIG. 13 is an illustration diagram showing conditions of a grating in the optical fiber sensor according to the third preferred embodiment of the present invention.

FIG. 14 is an illustration diagram showing conditions of a grating in the optical fiber sensor according to the third preferred embodiment of the present invention.

FIG. 15 is an illustration diagram showing conditions of a grating in the optical fiber sensor according to the fourth preferred embodiment of the present invention.

FIG. 24 is a schematic diagram showing gratings of the optical fiber sensor according to the eighth preferred embodiment of the present invention.

FIG. 25 is a graph showing a transmitted light spectra obtained from the optical fiber sensor according to the eighth preferred embodiment of the present invention.

BEST MODE FOR CARRYING OUT THE INVENTION

The First Preferred Embodiment

Figure 1:
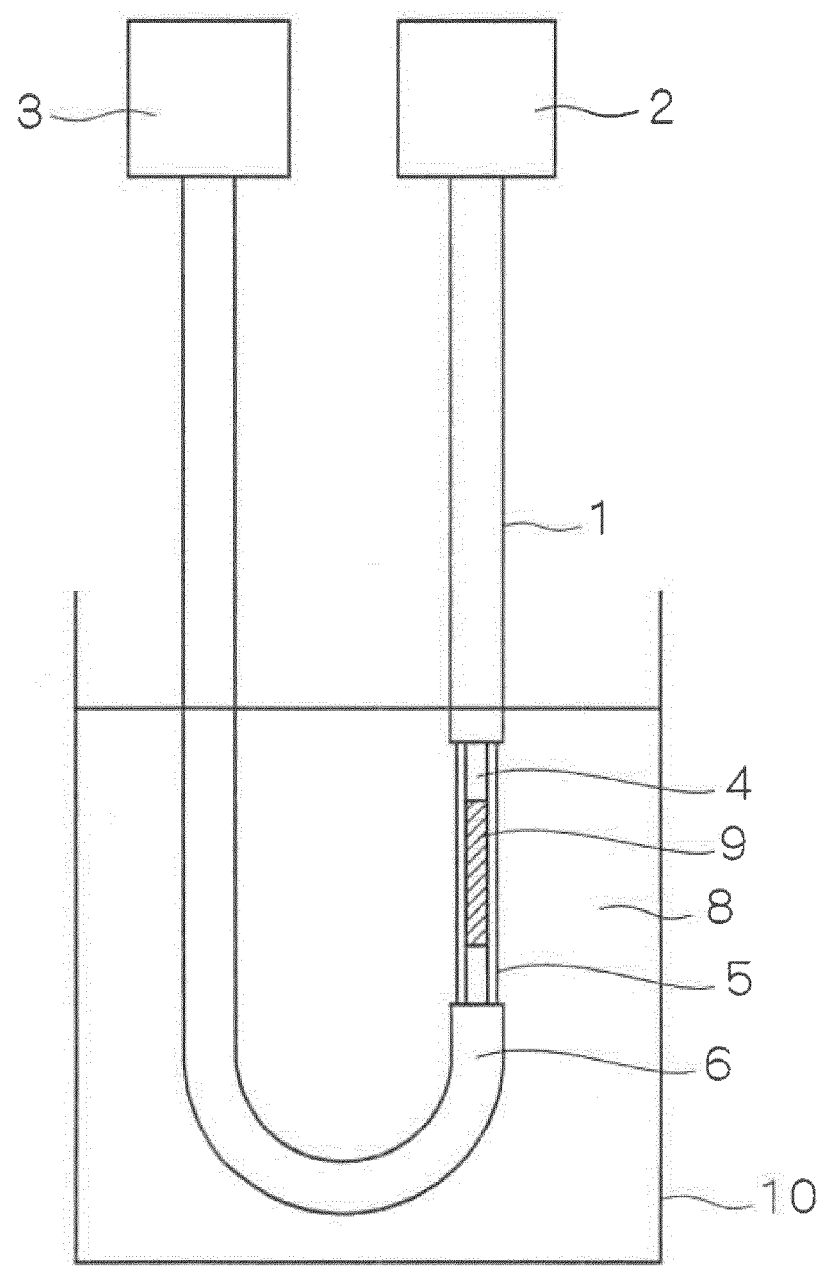
FIG. 1 is a schematic diagram showing an optical fiber sensor according to the first preferred embodiment of the present invention.

FIG. 1 is a schematic diagram showing an optical fiber sensor in accordance with the first preferred embodiment of the present invention. The optical fiber sensor shown in FIG. 1 is a sensor capable of detecting a refractive index of liquid. In the optical fiber sensor of FIG. 1, at an end of an optical fiber 1, a light source 2 is arranged and at the other end thereof, a light receiving part 3 is arranged. The optical fiber 1 comprises a core 4 propagating light emitted from the light source 2, a cladding 5 which is so provided as to cover the core 4 so that the light may be enclosed in the core 4 and a fiber jacket 6 covering and protecting these parts.

Further, in the optical fiber 1, for measurement of refractive index of liquid, part of the fiber jacket 6 is removed so that a liquid 8 which is a medium to be measured may come into direct contact with the cladding 5. Furthermore, in the optical fiber 1 of FIG. 1, a Bragg grating (hereinafter, sometimes referred to as "grating") 9 is formed in the core 4 at a portion where part of the fiber jacket 6 is removed. This optical fiber 1 is bent in a "U" shape near a bottom surface of a container 10 storing the liquid 8 and the light source 2 and the light receiving part 3 are arranged outside the container 10.

As the light source 2, for example, a light emitting diode (LED), a super luminescent diode (SLD) and the like can be used. On the other hand, the light receiving part 3 uses a light receiving element such as a photodiode and the like to detect the received light intensity. As the core 4 and the cladding 5, inorganic glass such as quartz glass and the like or a plastic-based material such as polymethyl methacrylate and the like can be used. As the fiber jacket 6, a fluorine-based, nylon-based, phenol-based, epoxy-based or melanin-based resin can be used.

Next, as a method of forming the grating 9 in the core 4, for example, a phase mask is provided at the portion where the fiber jacket 6 is removed, and irradiated with an excimer laser beam, to thereby form a pattern of grating corresponding to a relief of the phase mask. The phase mask is a mask in which a plurality of grooves, which is called "relief", are formed at regular intervals on one-side surface of parallel planes made of quartz glass, and the laser beam is periodically modulated by the relief.

Since a photo-induced refractive index change is caused in the core 4, where the refractive index of a portion irradiated with the laser beam becomes higher than that of an unirradiated portion, it is possible to form the grating 9 in which the refractive index periodically changes in the core 4. By changing the pitch of the relief and the depth of the groove, the grating 9 having a desired pattern can be formed in the core 4. Further, by tilting the phase mask toward the inplane direction, it is possible to form the grating 9 having a tilt angle.

Gratings 9 are generally classified into a short-period grating having a refractive index change period of about 0.1 to 1 μm and a long-period grating having a period of 100 to 1000 μm. The grating 9 used in the present invention is limited to the former, i.e., the short-period grating, and each grating in the following description refers to a short-period grating.

Next, discussion will be made on an operation of the optical fiber sensor in accordance with the first preferred embodiment. In an optical communications system, generally, in order to take out optical signals of a specific wavelength propagating in an optical fiber transmission line, a grating capable of reflecting only specified signals is used. The transmission properties of the grating has a cladding propagation mode discussed later and this cladding propagation mode disadvantageously becomes the loss ripple. The present invention conversely utilizes this cladding propagation mode which has been considered as a needless property in the optical communications system.

The principle for measurement of the refractive index of the liquid 8 shown in FIG. 1 utilizes the fact that the intensity of light, referred to as "cladding propagation mode", which is caused when the light propagating in the core 4 is reflected on the grating 9 or passes through the grating 9, depends on the refractive index of a material which is in contact with the outer side of the cladding 5. Specifically, the light propagating in the core 4 propagates only in the core 4, repeating reflection at the interface between the core 4 and the cladding 5 in a portion where no grating 9 is formed. When the light propagating in the core 4 reaches the grating 9, however, the light is divided into light which is to pass through the grating 9 and propagate in the core 4, light to be Bragg-reflected on the grating 9 and propagate in the core 4 in the opposite direction and light of backward propagation cladding propagation mode which is to jump out of the core 4 and propagate in the cladding 5 in the opposite direction. In the short-period grating used in the optical fiber sensor of FIG. 1 the cladding propagation mode is backward propagation, but the cladding propagation mode generated in the long-period grating is forward propagation.

FIGS. 2(a) and 2(b) are views showing a relation between the light in the cladding propagation mode and the refractive index of the liquid which is in contact with the outer side of the cladding 5. In the following discussion, water is taken as an example of liquid and air is taken as an example of gas. FIG. 2(a) schematically shows the propagation of light in a case where the material which is in contact with the outer side of the cladding 5 is air 21, and FIG. 2(b) schematically shows light propagation in a case where the material which is in contact with the outer side of the cladding 5 is water 27. It is assumed, herein, that the refractive index of the air 21 is 1.0, the refractive index of water 27 is 1.3, the refractive index of the core 4 is 1.36 and the refractive index of the cladding 5 is 1.35.

In FIG. 2(a), a propagation light 22 propagating from the light source 2 is divided into a reflected light 23 which is Bragg-reflected on the grating 9, a transmitted light 24 passing through the grating 9 and propagating in the core 4 and a light 25 in the cladding propagation mode which is generated in the grating 9. Since the difference between the refractive index of the cladding 5 and that of the air 21 is large, 0.35, the light 25 in the cladding propagation mode is reflected on an interface 26 between the cladding 5 and the air 21 and propagates in the cladding 5. In FIG. 2(a), since the light 25 in the cladding propagation mode is enclosed in the cladding 5, there appears a loss ripple typical of the cladding propagation mode in the transmission properties.

On the other hand, also in FIG. 2(b), the propagation light 22 propagating from the light source 2 is divided into the reflected light 23, the transmitted light 24 and the light 25 in the cladding propagation mode. However, in the case of FIG. 2(b), since the difference between the refractive index of the cladding 5 and that of the water 27 is small, 0.05, the light 25 in the cladding propagation mode, which is generated at an end portion of the grating 9, is hardly reflected on an interface 28 between the cladding 5 and the water 27, passing through the interface 28, and propagates to the water 24. For this reason, the light 25 in the cladding propagation mode hardly propagates in the cladding 5. Therefore, no light 25 in the cladding propagation mode is enclosed in the cladding 5 and there appears no loss ripple which is a transmission property typical of the cladding propagation mode.

Figure 3:
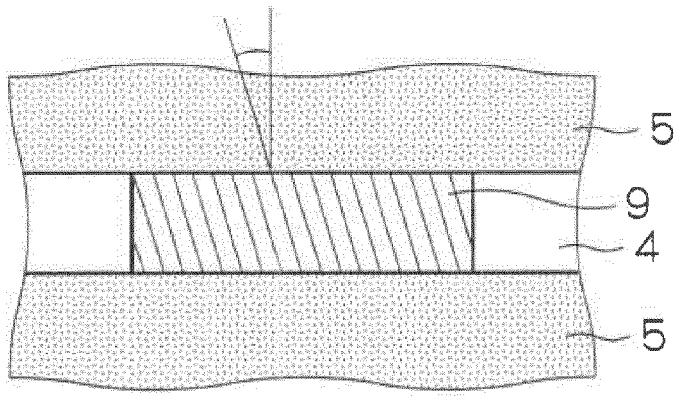
FIG. 3 is an illustration diagram showing the tilt angle of a grating in the optical fiber sensor according to the first preferred embodiment of the present invention.

Further, the grating 9 of the first preferred embodiment is so formed as to have a tilt angle of θ° with respect to a vertical line in a longitudinal direction of the optical fiber 1 as shown in FIG. 3, for the purpose of obtaining a sensor output with high sensitivity and enlarging a detection range of refractive index of a medium to be measured. The tilt angle θ° is determined in a range not lower than −90° and lower than 90°. FIGS. 4(a) to 4(d) show wavelength spectra of transmission losses in a case where the tilt angle θ is set to 0°. The optical fiber 1 used in this case is made of quartz-based material, having a cladding diameter of 125 μm and a core diameter of 2 μm.

FIG. 4(a) shows a case where a medium to be measured is air (n=1.0), and FIG. 4(b) shows a case where a medium to be measured is ethanol (n=1.362). FIG. 4(c) shows a case where a medium to be measured is a liquid (n=1.429) containing 50% of ethanol and 50% of toluene, and FIG. 4(d) shows a case where a medium to be measured is toluene (n=1.497). The media to be measured shown in FIGS. 4(a) to 4(d) have different refractive indices, and in the case of using the medium whose refractive index is small, such as air or ethanol, the cladding propagation mode noticeably appears in the range where the wavelength ranges from 860 nm to 885 nm. However, as the refractive index becomes larger, (FIGS. 4(c) and 4(d)), the cladding propagation mode disappears from the low wavelength side, and in the case of using toluene, (FIG. 4(d)), the cladding propagation mode completely disappears.

Figure 4:
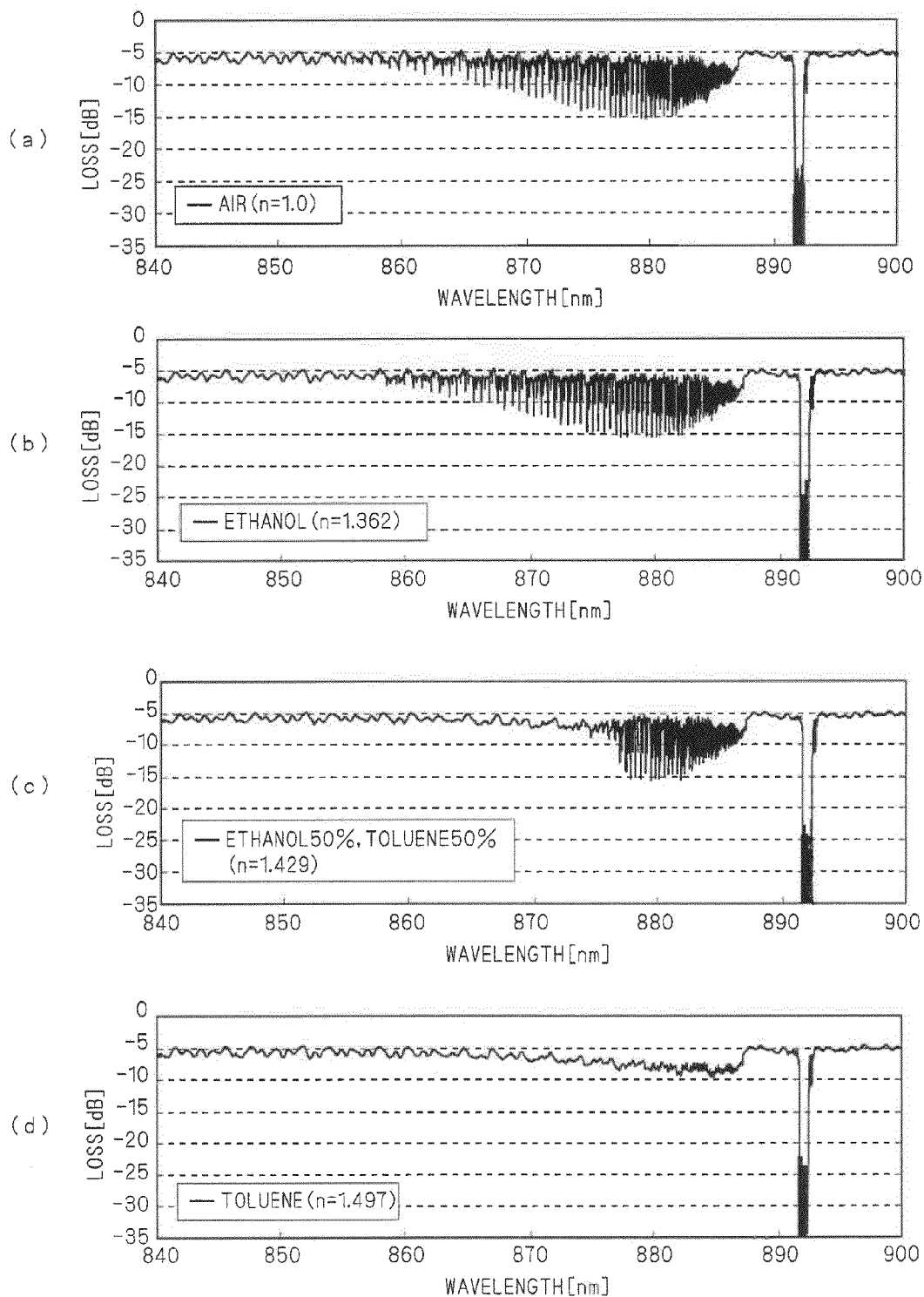
FIG. 4 is a diagram showing wavelength spectra of transmission losses in the optical fiber sensor according to the first preferred embodiment of the present invention.
Figure 5:
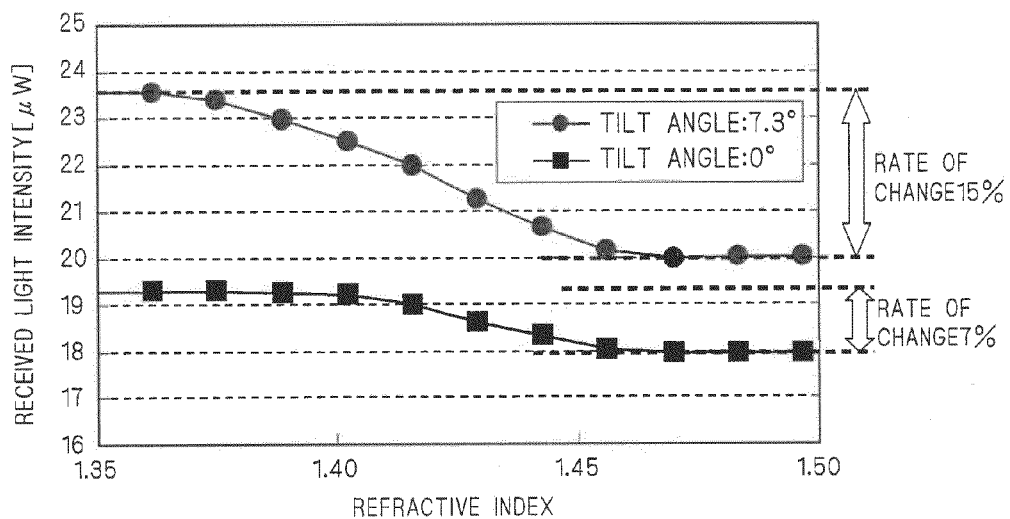
FIG. 5 is an illustration diagram showing a relation between a refractive index and the received light intensity in the optical fiber sensor according to the first preferred embodiment of the present invention.

The optical fiber sensor shown in FIG. 1 has a construction to detect the transmitted light shown in FIG. 4 as the received light intensity. Therefore, the optical fiber sensor of FIG. 1 detects the refractive index of a medium to be measured by utilizing the change in the received light intensity depending on the refractive index of the medium to be measured, as shown in FIG. 5. FIG. 5 shows the change of the received light intensity with respect to the refractive index between the case where the tilt angle θ of the grating 9 is 0° and the case where the tilt angle θ is 7.3°. As shown in the result of FIG. 5, the refractive index detection range of the medium to be measured is enlarged and the rate of change increases in the case where the tilt angle θ is 7.3° as compared with the case where the tilt angle θ is 0°.

As to the refractive index detection range of the medium to be measured, as shown in FIG. 5, on the high refractive index side, the refractive index is about 1.46 in the both cases where the tilt angle θ is 0° and 7.3°, but on the low refractive index side, while the refractive index is 1.40 in the case where the tilt angle θ is 0°, the refractive index is enlarged up to about 1.36 in the case where the tilt angle θ is 7.3°. Therefore, the optical fiber sensor in which the tilt angle θ of the grating 9 is 7.3° can be used to detect, e.g., the blended fuel of regular gasoline (n=1.43) and ethanol (n=1.362). Further, the rate of change is 7% when the tilt angle θ is 0°, but when the tilt angle θ is 7.3°, the rate of change increases up to 15%. The increase in the rate of change leads to an increase in reliability of the optical fiber sensor against environmental changes such as oscillation, temperature variation and the like.

Figure 6:
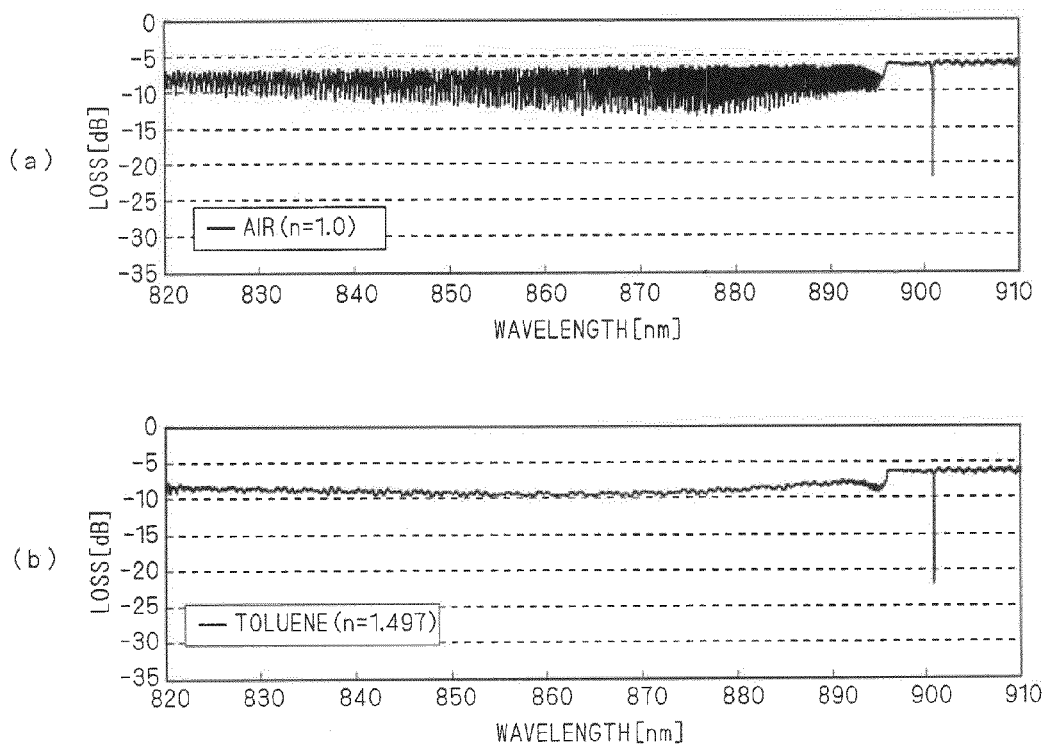
FIG. 6 is a diagram showing wavelength spectra of transmission losses of air and toluene in the optical fiber sensor according to the first preferred embodiment of the present invention.

Further, preparing optical fiber sensors having the gratings 9 with various tilt angles, wavelength spectra of transmission losses are measured in the cases where the cladding propagation mode appears (air: n=1.0) and where it disappears (toluene: n=1.497). FIGS. 6(a) and 6(b), for example, show the wavelength spectra of the transmission losses in the case where the tilt angle of the grating 9 is 11.7°. While the cladding propagation mode appears in the case where the medium to be measured is air as shown in FIG. 6(a), the cladding propagation mode completely disappears in the case where the medium to be measured is toluene as shown in FIG. 6(b).

The rate of change of received light intensity is calculated from the wavelength spectra of transmission losses of the each case where the medium to be measured is toluene and air, and the rate of change with respect to the tilt angle of the grating 9 is plotted in FIG. 7. From the result shown in FIG. 7, it is found that the rate of change increases as the tilt angle θ of the grating 9 becomes larger.

Next, transmission wavelength spectra of regular gasoline and high-octane gasoline are shown in FIGS. 8(a) and 8(b). As shown in FIG. 8(a), in the case of regular gasoline, transparent regions appear when the wavelength is in the ranges from 500 nm to 1100 nm, from 1250 nm to 1350 nm and from 1500 nm to 1600 nm. As shown in FIG. 8(b), in the case of high-octane gasoline, transparent regions appear when the wavelength is in the ranges from 450 nm to 1100 nm, from 1250 nm to 1350 nm and from 1500 nm to 1600 nm.

Though the light source 2 having a 800-nm band is used in the first preferred embodiment, also the other transparent regions of the medium to be measured may be used to realize this preferred embodiment. For example, a light source 2 and a light receiving part 3 which have a 1500-nm band that is commonly used in the optical communication may be also used. In addition, since there arises a loss due to light absorption in a region other than the transparent region, it is desirable that detection should be made in the transparent region of the medium to be measured.

Though the grating 9 of refractive index modulation type in which the refractive index periodically changes is used in the optical fiber sensor of the first preferred embodiment, a grating 9 processed so that grooves are periodically arranged may be used.

Figure 9:
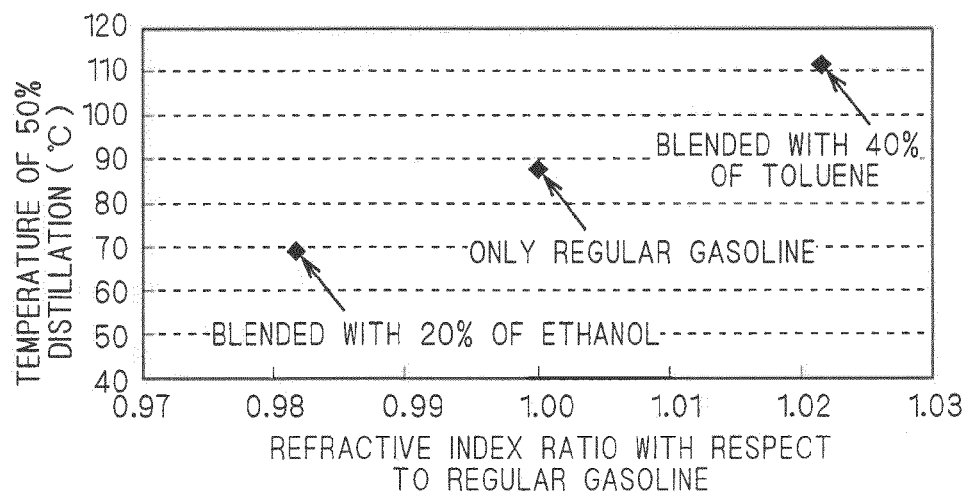
FIG. 9 is an illustration diagram showing characteristics of blended gasoline.

As described in the Background Art, whether the gasoline is heavy or light is correlated with its refractive index, and the heavy gasoline has a large refractive index and the light gasoline has a small refractive index. More specifically. FIG. 9 shows the respective relations between the refractive index ratio with respect to regular gasoline and the distillation property in the cases of regular gasoline, regular gasoline blended with 20% of ethanol and regular gasoline blended with 40% of toluene. As shown in FIG. 9, when blended with toluene, the refractive index ratio is large and the 50% capacity temperature is also large, and so this gasoline is heavy gasoline. On the other hand, as shown in FIG. 9, when blended with ethanol, the refractive index ratio is small and the 50% capacity temperature is also small, and so this gasoline is light gasoline.

The Second Preferred Embodiment

In the optical fiber sensor of the first preferred embodiment, it has made clear that it is desirable that a grating having a tilt angle which causes large change of received light intensity should be used in order to measure the refractive index of the medium to be measured with sufficient sensitivity even if a cheap detecting electric circuit is used. Further, in the second preferred embodiment, discussion will be made on a grating having a tilt angle which has conditions for an increase of the change in the received light intensity.

In each case that the optical fiber sensor is immersed in a low refractive index medium such as air and a high refractive index medium such as toluene, the spectra in the cladding propagation mode are shown in FIGS. 6(a) and 6(b). In the case of the low refractive index medium, while there are a plurality of sharp transmission loss peaks due to the cladding propagation mode in the case of the high refractive index medium, the sharp transmission loss peak disappears and a continuous transmission loss spectrum appears. In the case of the high refractive index medium, since light reflection on an interface between the cladding and the medium becomes small, the core propagation mode is coupled to a continuous emission mode made toward the surrounding space through the grating 9, not to the cladding propagation mode, making a continuous spectra shape.

There is a quantitative correlation between the transmission loss spectrum having a sharp peak of the cladding propagation mode in the case of the low refractive index medium and the continuous transmission loss spectrum in the case of the high refractive index medium. Specifically, there is a sum rule and it is experimentally verified that the average amount of loss intensity of spectra over a certain wavelength range is almost the same between the respective transmission loss spectra of these media.

In the measurement of the quantity of transmitted light using continuous spectrum light source of wide wavelength band, in the case of the low refractive index medium, the transmitted light in a wavelength range with large transmission factor existing between adjacent transmission loss peaks is a main element of the quantity of transmitted light. Even if the lithographic quantity of lithographic exposure the grating 9 increases to increase the intensity of the transmission loss peak, the quantity of transmitted light in the wavelength range with large transmission factor hardly decreases. Therefore, a decrease in the total quantity of transmitted light is suppressed. On the other hand, in the case of the high refractive index medium, since the quantity of transmitted light decreases in accordance with the transmission loss intensity, not largely depending on the wavelength, an increase in the lithographic quantity of lithographic exposure the grating 9 increases the transmission loss and decreases the quantity of transmitted light. Thus, the quantity of transmitted light in the case of the high refractive index medium is smaller than that in the case of the low refractive index medium which has a nonuniform transmission loss spectrum.

Therefore, in order to increase the change in the quantity of detected light to measure the refractive index with high sensitivity in the optical fiber sensor, it is effective that the quantity of transmitted light in the case of the spectra with a sharp peak is increased and the transmission loss intensity in the case where the continuous spectra shape appears is increased.

Figure 10:
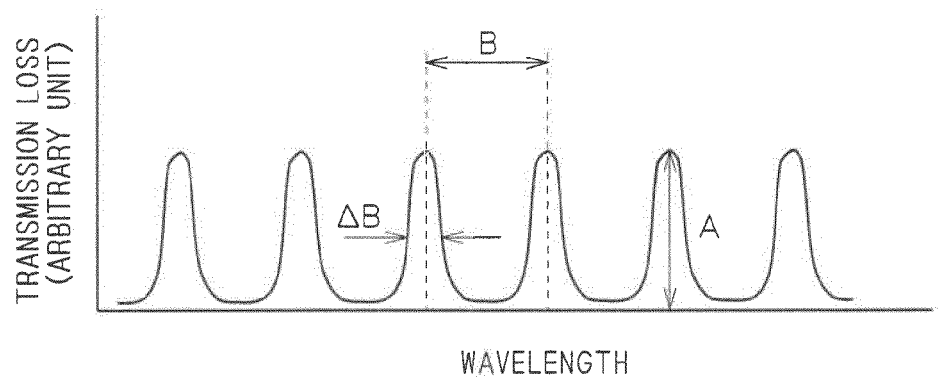
FIG. 10 is an illustration diagram showing the transmission loss in an optical fiber sensor in the optical fiber sensor according to the second preferred embodiment of the present invention.

Next, discussion will be made on a result of quantitative trial calculation performed on the change in the quantity of detected light by assuming a model. First, the premise of the considered model will be discussed, referring to FIG. 10. FIG. 10 is a view schematically showing a parameter of the cladding propagation mode. First, since it is necessary to detect a refractive index of wide range including the refractive index range required by the medium to be measured, it is assumed that the size of the refractive index range is a detection range Δn. It is assumed that the cladding propagation mode uniformly appears in the range between the wavelengths which correspond to the lower limit and the upper limit of the detection range Δn.

By using a continuous wavelength light source including the wavelengths in the detection range Δn, the total transmitted light intensity is detected. It is assumed that, with respect to all the cladding propagation modes included in the detection range Δn, an average magnitude of the transmission loss peaks is AdB, an average value of the full widths at half maximum of the loss peaks is ΔBnm and an average wavelength interval of the loss peaks is Bnm. In the case of a spectrum having a sharp peak, it is assumed that the loss peak in the cladding propagation mode and the spectra shape of the light source have a rectangular shape and the same loss intensity, for simplification, and that the transmission loss in a transmission wavelength region between the loss peaks of the adjacent cladding propagation modes is zero.

Under the above assumption, the rate of appearance of the transmission loss in the cladding propagation mode is ΔB/B and the rate of appearance of a transparent wavelength range is 1-ΔB/B. In the case of the low refractive index medium, since the cladding propagation mode of the transmission loss AdB and the transparent wavelength range coexist, the transmitted light intensity is given by Eq. 1:

$$I_1 = 1 - \frac{\Delta B}{B} + \frac{\Delta B}{B} \cdot 10^{-\frac{A}{10}} \quad \text{(Eq. 1)}$$

On the other hand, in the case of the high refractive index medium, since the averaged transmission loss is A×ΔB/BdB in the whole wavelength range, the transmitted light intensity is given by Eq. 2:

$$I_2 = 10^{-\frac{A}{10} \cdot \frac{\Delta B}{B}} \quad \text{(Eq. 2)}$$

From the above, the rate of change in the quantity of transmitted light is given by I=(I₁-I₂)/I₁.

Figure 11:
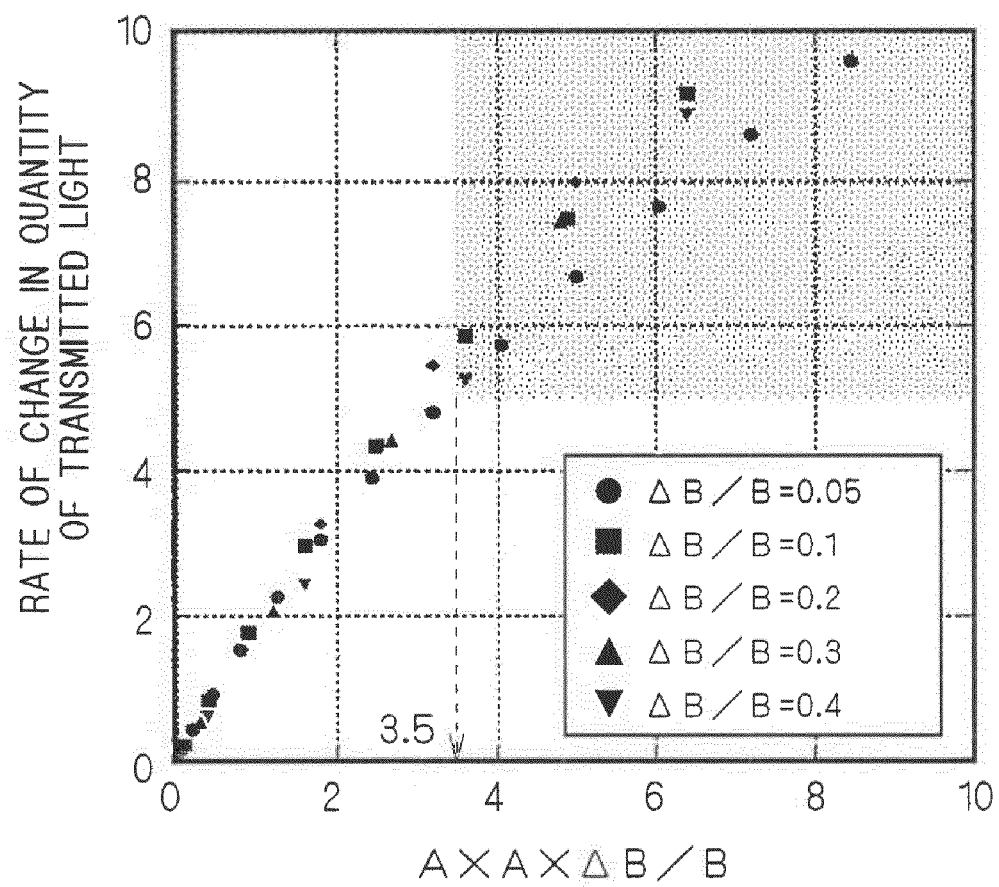
FIG. 11 is an illustration diagram showing conditions of a grating in the optical fiber sensor according to the second preferred embodiment of the present invention.

FIG. 11 shows a result of calculation for the change ratio I of the quantity of transmitted light in the range of 1≦A≦15 and 0.05≦ΔB/B≦0.4. From numerical calculations performed with respect to various values A and ΔB/B, it is found that the change ratio I of quantity of transmitted light almost depends on A×A×ΔB/B. This matches the lowest order term. A×A×ΔB/B, in the case where the equation for the change ratio I of the quantity of transmitted light is expanded in a series with respect to A and ΔB/B.

The above discussion is made on the result of calculation for the change ratio I of the quantity of transmitted light in the cases of the low refractive index medium (where all cladding propagation mode peaks appear) and the high refractive index medium (where all cladding propagation mode peaks disappear). In the case of the medium to be measured having a medium refractive index, the cladding propagation mode disappears from the short wavelength side as the refractive index increases, and the quantity of transmitted light simply and continuously changes between the result in the case of the low refractive index medium and that in the case of the high refractive index medium. Therefore, even in the case of the medium to be measured having a medium refractive index, by obtaining revised data in advance, it is possible to know the refractive index of the medium to be measured from the detection of the quantity of transmitted light.

The sensitivity of measurement for the refractive index is proportional to the change ratio I of the quantity of transmitted light. Though it is possible to perform the measurement in principle by precisely measuring an output signal voltage even if a grating with low sensitivity having a small change ratio I of the quantity of transmitted light is used, a measuring electric circuit becomes more expensive and a measurement time increases since integration is needed. Further, if the grating with low sensitivity having the small change ratio I of the quantity of transmitted light is used, this causes some problems such as the need for a regular revision work because of the change with the passage of time in output signal itself, and the like. If the change ratio I of the quantity of transmitted light of 5% or more is obtained, it is thought that the above problem can be avoided. From FIG. 11, it is found the change ratio I of the quantity of transmitted light=5% is corresponding to A×A×ΔB/B=3.5.

Though the above discussion is made on a simplified model, it is confirmed that the result of actual measurement is well reproduced. For example, the change ratio I of the quantity of transmitted light is about 7% in an actually-manufactured grating having ΔB/B≦0.3, a transmission loss≦4 dB and a tilt angle of 0°. This value almost coincides with the value obtained by calculation and this corroborates the validity of this model.

Thus, in the optical fiber sensor of the second preferred embodiment, in order to have the change ratio I of the quantity of detected light with which the refractive index of the medium to be measured can be measured with sufficient sensitivity even if a cheap detecting electric circuit is used, the grating has a relation of A×A×ΔB/B≧3.5. In FIG. 11, the range satisfying A×A×ΔB/B≧3.5 is expressed with hatching.

As to the full width at half maximum ΔB of the loss peak in the cladding propagation mode, though there may be influences of nonuniform shape of the optical fiber and whether the length of the grating is long or short and the like, but actually, nonuniform line width due to the quality of irradiation light, positional fluctuation, optical fiber distortion in exposure and the like is predominant. Therefore, by forming a uniform grating with the fluctuation suppressed, it is thought that a cladding propagation mode with a narrow line width can be obtained.

The interval B between each loss peak of the cladding propagation modes generally depends on the cladding diameter and the used wavelength in the optical fiber, and the shorter the used wavelength becomes or the larger the cladding diameter becomes, it is thought that the mode interval becomes smaller. When an optical fiber having a diameter of 125 μm, which is generally prevalent, is used, the cladding diameter is fixed. As to the used wavelength, since the full width at half maximum ΔB is small, like the interval B, even if the wavelength is short, it is thought that there is not large difference in ΔB/B.

The transmission loss A of the loss peak in the cladding propagation mode increases as the quantity of lithographic exposure in the grating increases and gradually becomes saturated. Further, the transmission loss A increases as the length of the grating increases. As to the relation with ΔB/B, with respect to the grating having certain quantity of lithographic exposure, the transmission loss A increases as the full width at half maximum ΔB in the cladding propagation mode becomes smaller, and it is thought that A×ΔB/B is generally constant.

From the above qualitative study, in manufacturing the grating, by increasing the quantity of lithographic exposure, performing highly uniform exposure with fluctuation suppressed and increasing the length of the grating, it is possible to obtain a highly sensitive grating having large A×A×ΔB/B.

As compared with a case of using the grating having a tilt angle of 0°, since the permitted number of cladding modes increases and ΔB/B increases by appropriately selecting the tilt angle of the grating, it is possible to further increase the refractive index detection sensitivity in proportion thereto. As the light source, a light emitting diode (LED) can be used and this is suitable for size reduction of the light source and an increase of reliability. Further, for detection of the transmitted light, a photodiode can be used. If a high-intensity light source such as a super luminescent diode (SLD) or the like is used, it is possible to measure the refractive index with higher precision. These light emitting element and light receiving element can be optically coupled to the optical fiber by using an appropriate coupling optical system in accordance with the numerical aperture of the optical fiber and can be constructed as a small-sized module.

On the basis of the above study, in manufacturing a grating with used wavelength of 800-nm band by using an optical fiber having a core diameter of 2 μm, for example, only if the grating length is 5 mm or more, it is possible to manufacture a grating having a relation of A×A×ΔB/B≧3.5 by controlling the exposure conditions. If the grating length is lengthened up to 10 mm or the like, it is possible to achieve a grating with higher sensitivity and increase the tolerance of the exposure conditions.

The Third Preferred Embodiment

In the third preferred embodiment, discussion will be made below on conditions required to manufacture the grating 9 with high sensitivity.

In the optical fiber sensor of the third preferred embodiment, it is possible to observe the loss peaks due to many cladding propagation modes, with the transmission spectra, regardless of whether the grating has a tilt or not. These cladding propagation modes are coupled to core propagation modes with different coupling strengths, and each shows loss intensity reflecting the coupling strength. In order to measure the refractive index of the medium to be measured by the optical fiber sensor shown in FIG. 1, it is necessary that the cladding propagation modes should continuously appear in the detection range of refractive index without a remarkable decrease in the loss intensity.

The spectra shape of the cladding propagation mode can be obtained through calculation by giving parameters on the optical fiber, such as the core diameter and the core refractive index, the cladding diameter and the cladding refractive index and the like, and parameters on the grating, such as the tilt angle, the pitch, the amount of change in the refractive index and the like.

Figure 12:
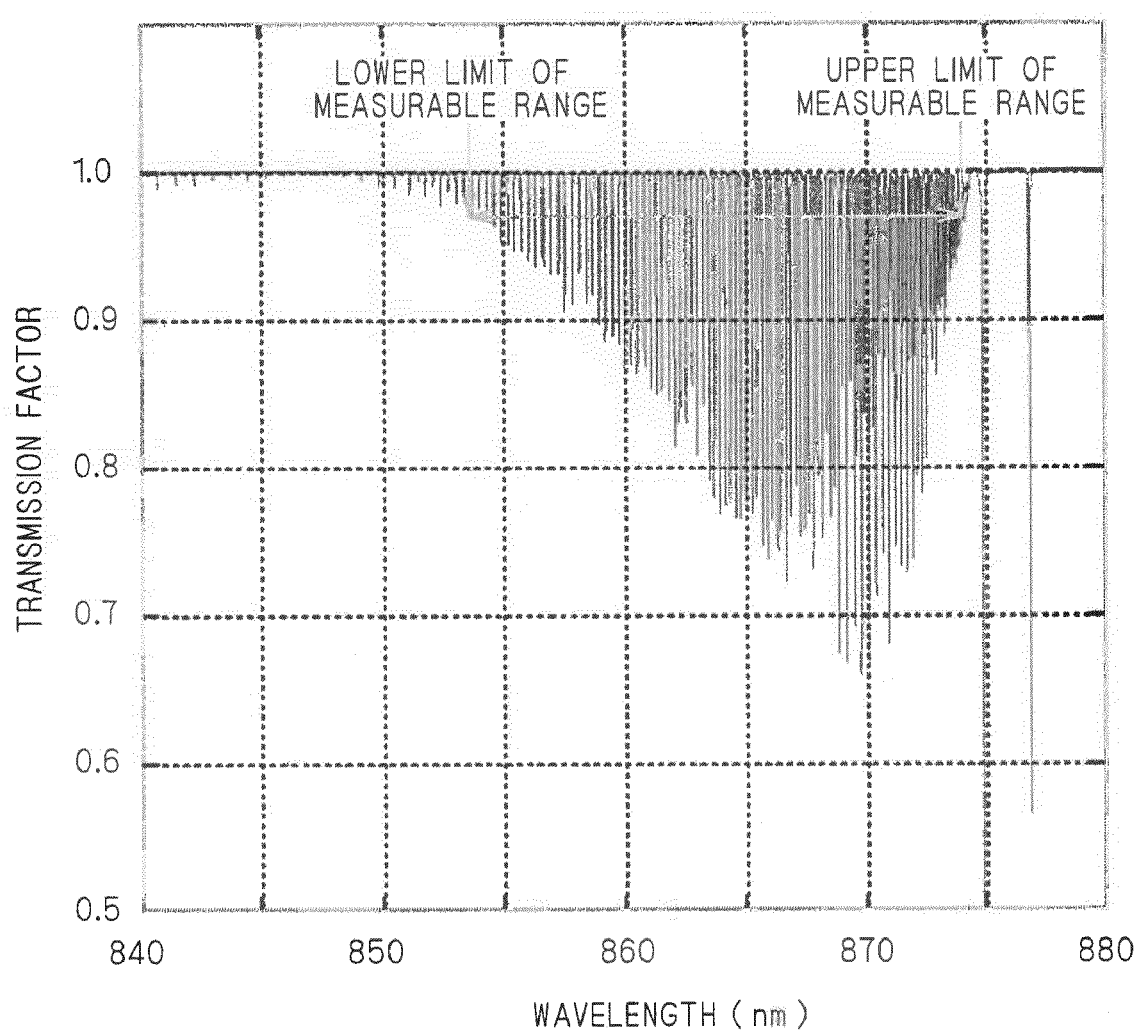
FIG. 12 is an illustration diagram showing the spectra shape in a cladding propagation mode.

First, assuming that the cladding diameter is 125 μm and the Bragg wavelength is λ=880±5 nm, the spectra shape of the cladding propagation mode in the case of changing the core diameter and the tilt angle of the grating is calculated to obtain an appearance wavelength range of the cladding propagation mode, and the range is converted into the range of refractive index and compared. The spectra shape of the cladding propagation mode has an envelope of the peak having a gently unimodal shape, and the wavelength which is one-tenth of the maximum value of the cladding propagation mode loss is regarded as the upper limit and lower limit wavelengths in the appearance wavelength range. One exemplary spectra shape of the cladding propagation mode obtained through the calculation (where the core diameter is 4 μm, the tilt angle is 6 and the Bragg wavelength is 880 nm) is shown in FIG. 12. It is assumed that the refractive index of the cladding is 1.4533, and the refractive index of the core is selected out of the range from 1.4830 to 1.4563, referring to specifications of commercial optical fibers that are purchasable.

The measurable range of refractive index which is obtained through the above calculation is plotted as a function of the tilt angle θ in FIG. 13. FIG. 13 shows relations between the measurable ranges of refractive index and the tilt angles with respect to different core diameters. From FIG. 13, it is found that the lower limit refractive index in the measurement range decreases as the tilt angle θ increases with respect to all the core diameters. Further, as to the core-diameter dependence, it is found, from FIG. 13, that the lower limit refractive index more significantly decreases as the core diameter becomes smaller.

On the other hand, the upper limit refractive index in the measurement range takes a value approximate to the refractive index of the cladding regardless of the core diameter in the case of small tilt angle as shown in FIG. 13, but decreases as the tilt angle increases. Further, a decrease in the upper limit refractive index in the measurement range is small when the core diameter d≦4 μm as shown in FIG. 13 but becomes larger when the core diameter becomes more than 4 μm. When the core diameter becomes larger, the decrease in the upper limit refractive index in the measurement range cancels enlargement of the measurement range due to a decrease in the lower limit refractive index in the measurement range, and measurement sensitivity with respect to the refractive index near the refractive index of the cladding decreases and it becomes difficult to perform a measurement near the refractive index.

Thus, in the case where the grating is formed so that the Bragg wavelength may be λ≦880 nm, in order to suppress the decrease in the upper limit refractive index in the measurement range and measure the refractive index in a wide range, the core diameter has only to be d≦4 μm.

Next, in the case where the Bragg wavelength of the grating is changed to λ≦1570 nm with which a light source is easily available in the optical communication wavelength range, the upper limit refractive index and the lower limit refractive index in the measurement range are calculated in the same manner. The result of this calculation is plotted as a function of the tilt angle in FIG. 14. In FIG. 14, two types of core diameters. 4 μm and 8 μm, are used.

As compared with the case of FIG. 13 where the Bragg wavelength is λ≦880 nm, it is found that in the result of FIG. 14, the properties are similar among the data whose d/λ have approximate values. Specifically, the result (d/λ=2.3) of (d, λ)=(2 μm, 880 nm) and the result (d/λ=2.6) of (d, λ)=(4 μm, 1570 nm) are similar. It is also found that the result (d/λ=4.5) of (d, λ)=(4 μm, 880 nm) and the result (d/λ=5.2) of (d, λ)=(8 μm, 1570 nm) are similar.

Further, the result of similar calculation in the case where the Bragg wavelength is λ≦1570 nm which is twice that in FIG. 13 is shown in FIG. 15. In the case shown in FIG. 15, the results of (d, λ)=(2 μm, 880 nm) and (d, λ)=(4 μm, 1670 nm) have the same d/λ, and the results of (d, λ)=(4 μm, 880 nm) and (d, λ)=(8 μm, 1670 nm) have the same d/λ. As can be seen from the result shown in FIG. 15, when the value of d/λ is same, the upper limit refractive index and the lower limit refractive index in the measurement range well coincides, even if the core diameters are different.

From the above result, it is thought that the envelope of the spectra shape in the cladding propagation mode almost depends on the value of d/λ which is the ratio mainly between the core diameter and the Bragg wavelength. On the other hand, though the ratios of the core diameter and the Bragg wavelength with respect to the cladding diameter change since the cladding diameter is fixed at 125 μm, the cladding diameter has a relatively small influence on the envelope of the spectra shape in the cladding propagation mode since the spectra shapes have high similarity.

Therefore, in order to form the grating with the decrease in the upper limit refractive index in the measurement range suppressed, capable of measuring the refractive index in a wide range, the optical fiber having the core diameter d has only to be selected so that the relation between the core diameter and a predetermined Bragg wavelength λ becomes d/λ≦4.5.

Similarly, in order to form the grating with the decrease in the upper limit refractive index in the measurement range suppressed, capable of measuring the refractive index in a wide range, the grating having the Bragg wavelength λ has only to be formed so that the relation between a predetermined core diameter d and the Bragg wavelength λ becomes d/λ≦4.5.

Though the grating is thus obtained in consideration of the calculation result in the case where the cladding diameter is 125 μm, since the cladding diameter has a relatively small influence on the envelope of the spectra shape in the cladding propagation mode, the grating is not limited by the size of the cladding diameter. Further, in the third preferred embodiment, though the refractive index of quartz glass is used as the refractive index of the cladding, the present invention is not limited to this but an optical fiber having a different refractive index may be used.

Thus, since the grating satisfying the condition d/λ≦4.5 is formed in the optical fiber sensor of the third preferred embodiment, the lower limit of the detectable range of refractive index (detection range) in the case where the tilt angle of the grating increases can be enlarged to a wide range and at the same time, the decrease in the upper limit of the detection range can be suppressed, and it is therefore possible to measure refractive index in wider range with simple construction by selecting the core diameter, the Bragg wavelength and the tilt angle of the grating.

The Fourth Preferred Embodiment

In the fourth preferred embodiment, discussion will be made below on conditions required to appropriately set the tilt angle θ° of the grating.

In the third preferred embodiment, it has been discussed that the detectable range of refractive index increases as the tilt angle increases. In FIG. 13, the detectable range of refractive index (detection range) can be obtained by determining the tilt angle θ and the ratio d/λ between the core diameter and the Bragg wavelength. Conversely, the tilt angle θ can be obtained from the ratio d/λ and the required detection range Δn. Actually, an approximate expression Eq. 3 can be obtained from the calculation result of FIG. 13 with respect to the data with d/λ 4.5 (d=2, 3, 4 μm).

$$\theta \geq 70 \times \Delta n + 1.8 \times d/\lambda - 8 \qquad (\text{Eq. 3})$$

Further, as shown in FIG. 15, since dependence of the detection range for the tilt angle almost depends on the value of d/λ also in the case of different Bragg wavelength and core diameter, the approximate expression Eq. 3 similarly holds. By adopting the tilt angle θ given by Eq. 3, it is possible to measure a refractive index range which is wider than the required detection range Δn.

Thus, in the optical fiber sensor of the fourth preferred embodiment, in order to obtain a predetermined detection range by using a predetermined optical fiber, the grating is formed with its tilt angle θ° adjusted to satisfy the condition of Eq. 3. The grating of the fourth preferred embodiment can thereby enlarge the lower limit of the detection range to a wider range and at the same time, the decrease in the upper limit of the detection range can be suppressed. Further, by using Eq. 3, it is possible to easily select an optimal tilt angle of the grating in the case where the core diameter and the Bragg wavelength are given and obtain an optimized grating.

The Fifth Preferred Embodiment

In the fifth preferred embodiment, discussion will be made on a construction of an optical fiber refractive index sensor (optical fiber sensor) applicable to a liquid property sensor capable of detecting a mixing ratio of ethanol-blended gasoline.

First, the ethanol-blended gasoline has a refractive index in a range from the refractive index of gasoline blended with 0% of ethanol to about 1.42. In proportion to an increase in the mixing ratio of ethanol, the refractive index monotonously decreases and approximates to a range from the refractive index of ethanol to 1.36. Therefore, if the refractive index range ranging from 1.36 to 1.42 can be measured at a room temperature, the mixing ratio of the ethanol-blended gasoline can be estimated.

The refractive index range, however, is a value at the room temperature and it is expected that there arises a change of about 0.02 in the refractive index per 50° C. when the temperature of measurement environment changes. Therefore, if the refractive index in a range from 1.34 to 1.44 can be measured, the mixing ratio of the ethanol-blended gasoline can be measured in a practically sufficient range of temperature.

The condition for measurement of the refractive index in the range from 1.34 to 1.44 can be read from FIG. 13. FIG. 13 shows a calculation example of the optical fiber having a quartz cladding used in a cheap general-purpose optical fiber and the range of refractive index from 1.34 to 1.44 is shown with hatching. If the Bragg wavelength is in a range of 800 nm≦λ≦900 nm, for example, the core diameter d has only to be in a range of 2 μm≦d≦4 μm.

At that time, the tilt angle needs to be changed in accordance with the core diameter and the minimum value of the tilt angle can be obtained from above Eq. 3. Since the upper limit refractive index to be measured is close to the refractive index of the quartz cladding, the maximum value of the tilt angle has to be not higher than 10° where the decrease of the upper limit refractive index in measurement is hard to be caused if d≦4 µm. Further, from the above result, an appropriate tilt angle is 4° when d=2 µm, 6° when d=3 µm and 8°≦θ≦10° when d=4 µm.

Since the above optical fiber sensor can be constituted of low-cost parts such as the optical fiber having the quartz cladding, a light emitting diode light source, a photodiode photodetector and the like, it is possible to achieve cost reduction. Further, if the light emitting diode light source is used, the quantity of light which can be coupled becomes larger as the core diameter becomes larger in the range of 2 µm≦d≦4 µm, and advantageously, it is therefore possible to perform a measurement with higher precision.

For an phenomenon where the refractive index changes depending on the difference in temperature of the media to be measured, such a measurement as discussed below is performed. Specifically, measurement data of refractive indices for different temperatures are acquired in advance in an assumed range of temperature, and a revised data list of the refractive indices and the mixing ratio of ethanol in various temperatures is acquired. The temperature is measured by another temperature sensor and matching is made with data of the refractive index measured by the optical fiber sensor, to obtain the mixing ratio. The above revised data list may be contained in a small-sized electronic circuit such as a microcomputer or the like. Further, by using an existing small-sized temperature sensor, it is possible to achieve a small-sized optical fiber sensor for measuring the mixing ratio of ethanol-blended gasoline with excellent practicality.

Thus, since the optical fiber sensor of the fifth preferred embodiment uses the grating satisfying the above condition (specifically, d/λ≦4.5, 2 µm≦d≦4 µm and 800≦λ≦900 nm), it is possible to measure the mixing ratio of ethanol-blended gasoline in a practically sufficient range of temperature even if the optical fiber having the quartz cladding is used. When the optical fiber sensor of the fifth preferred embodiment is used, for example, its part with the grating formed is contained in a pipe of a fuel supply pump of a motorcar engine.

The Sixth Preferred Embodiment

As discussed in Background Art, whether the gasoline is heavy or light is correlated with its refractive index, and the heavy gasoline has a large refractive index and the light gasoline has a small refractive index. More specifically, FIG. 9 shows the respective relations between the refractive index ratio with respect to regular gasoline and the distillation property in the cases of regular gasoline, regular gasoline blended with 20% of ethanol and regular gasoline blended with 40% of toluene. As shown in FIG. 9, when blended with toluene, the refractive index ratio is large and the 50% distillate temperature is also large, and so this gasoline is heavy gasoline. On the other hand, as shown in FIG. 9, when blended with ethanol, the refractive index ratio is small and the 50% distillate temperature is also small, and so this gasoline is light gasoline.

Figure 16:
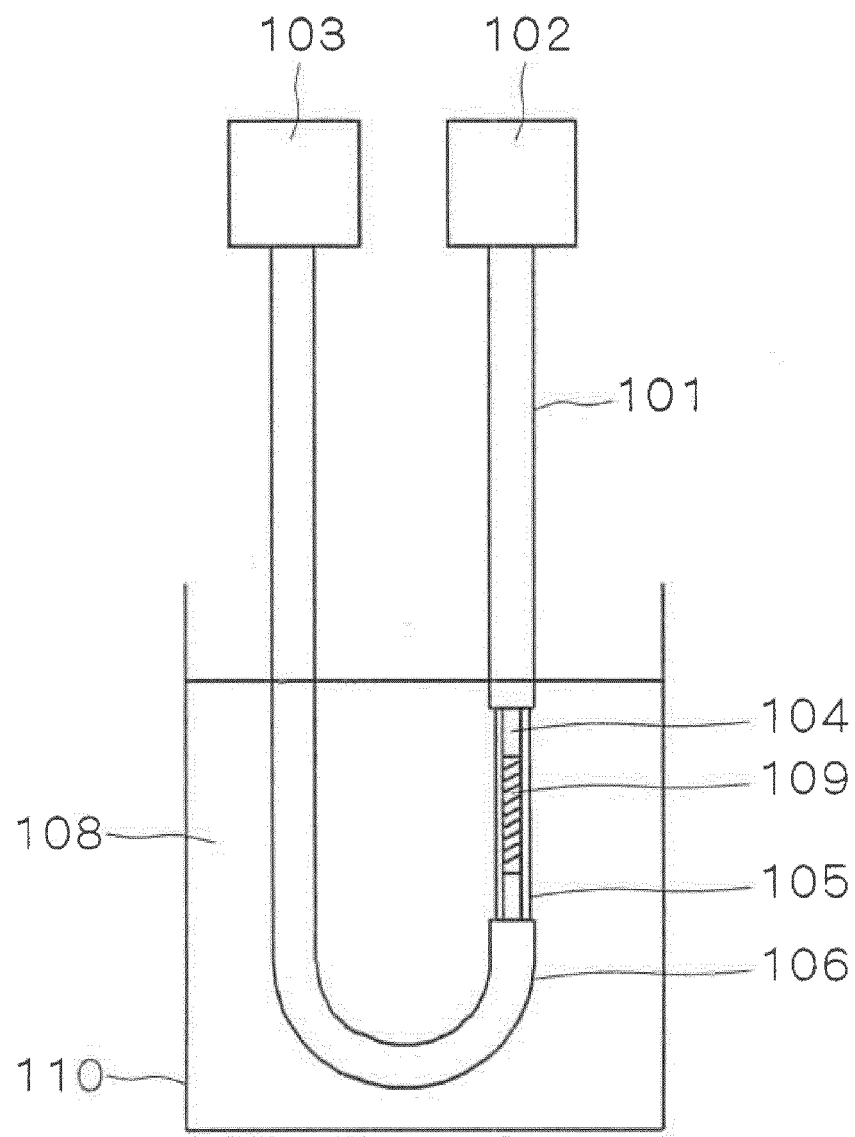
FIG. 16 is a schematic diagram showing the optical fiber sensor according to the sixth preferred embodiment of the present invention.

FIG. 16 is a schematic diagram showing an optical fiber sensor in accordance with the sixth preferred embodiment. The optical fiber sensor shown in FIG. 16 is a sensor for judging the property (for example, whether gasoline is heavy or light, or the like) of the medium to be measured by detecting the refractive index of the liquid which is the medium to be measured. In the optical fiber sensor of FIG. 16, at an end of an optical fiber 101, a light source 102 is arranged and at the other end thereof, a light receiving part 103 is arranged. The optical fiber 101 comprises a core 104 propagating light emitted from the light source 102, a cladding 105 which is so provided as to cover the core 104 so that the light may be enclosed in the core 104 and a fiber jacket 106 covering and protecting these parts. As the optical fiber 101, used is a core Ge-doped quartz multimode optical fiber of the graded index type with a core diameter of 62.5 µm and a cladding diameter of 125 µm.

Further, in the optical fiber 101, for measurement of the refractive index, part of the fiber jacket 106 is removed so that a liquid 108 which is a medium to be measured may come into direct contact with the cladding 105. Furthermore, in the optical fiber 101 of FIG. 16, a Bragg grating (hereinafter, sometimes referred to as "grating") 109 in which the refractive index changes with a period Λ of 0.3 µm is formed in the core 104 at a portion where part of the fiber jacket 106 is removed. The grating 109 having a tilt angle of 7.3° with respect to a vertical line in a longitudinal direction of the optical fiber is formed in a range of 10 mm. The optical fiber is subjected to processing for two weeks in a high pressure hydrogen atmosphere (at 100 atmospheric pressure) and irradiated with Nd-YAG laser (output of 200 mW, wavelength of 266 nm), to form the grating 109 therein. The tilt angle is determined in a range not lower than −90° and lower than 90°.

The optical fiber 101 shown in FIG. 16 is bent in a "U" shape near a bottom surface of a container 110 storing the liquid 108 and the light source 102 and the light receiving part 103 are arranged outside the container 110. As the light source 102, a light emitting diode (LED) is used and as the light receiving part 103, a photodiode is used.

Figure 17:
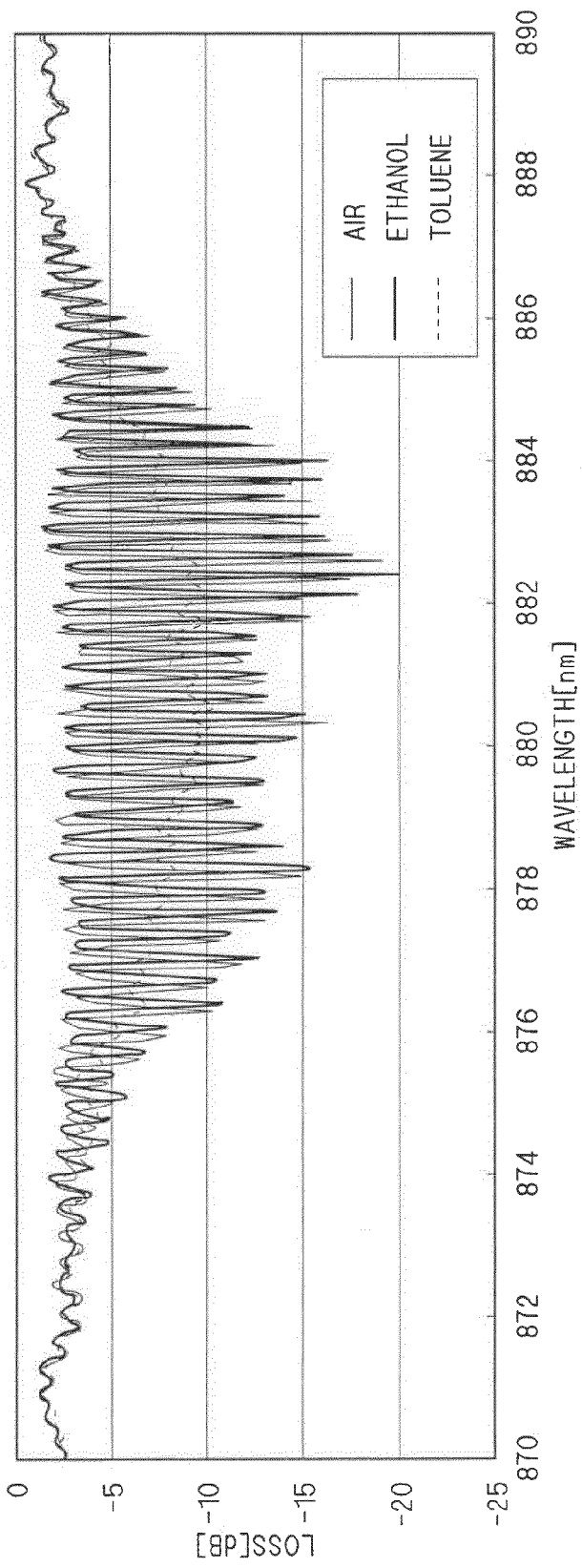
FIG. 17 is a graph showing a transmitted light spectra obtained from the optical fiber sensor according to the sixth preferred embodiment of the present invention.

FIG. 17 shows a transmitted light spectra of the optical fiber sensor in accordance with the sixth preferred embodiment. The transmitted light spectra shown in FIG. 17 is the spectra of the optical fiber sensor having a construction in which a multimode optical fiber is used as the optical fiber 101 and the grating 109 having the tilt angle of 7.3° is formed. Therefore, in the transmitted light spectra of FIG. 17, there arises no strong transmission loss due to Bragg reflection which is a mode where light is enclosed in the core 104 near the Bragg wavelength (about 0.9 µm) obtained by multiplying the period Λ by 2n/cos θ (the refractive index of the core 104 is n, the tilt angle is θ) and reflected.

Further, in the transmitted light spectra of FIG. 17, the mode where light of specific wavelength near the wavelength of 0.88 µm which is shorter than the Bragg wavelength propagates in the core 104 changes to the cladding propagation mode (hereinafter, referred to simply as "cladding mode") where the light is enclosed in the cladding 105, and there consequently arises a periodic and sharp transmission loss peak.

As the refractive index of the liquid 108 which is the medium to be measured becomes closer to the refractive index of the cladding 105, the light becomes harder to be enclosed in the cladding 105. In the transmitted light spectra of FIG. 17, as the refractive index becomes closer to the refractive index of the cladding 105, the cladding mode disappears from the low-wavelength side. In the transmitted light spectra of the case where toluene having a refractive index of 1.497 is used as the medium to be measured, as shown in FIG. 17, there is no sharp peak and there arises a gentle radiation loss with a small wavelength dependence.

An output of the light receiving part 103 is in proportion to the product of the transmitted light spectra of the optical fiber 101 and a light intensity spectra of the light source 102, which enters the core 104. In a case of using the light source 102 having the light intensity spectra which overlaps the wavelength generated in the cladding mode, the received light intensity of the light receiving part 103 changes depending on the difference between the cladding mode and the radiation mode and the received light intensity becomes larger if there is a cladding mode. Therefore, from the change in the received light intensity of the light receiving part 103, it is possible to obtain the refractive index of the liquid 108 which is the medium to be measured which is in contact with the cladding 105 at a region where the grating 109 is formed.

Figure 18:
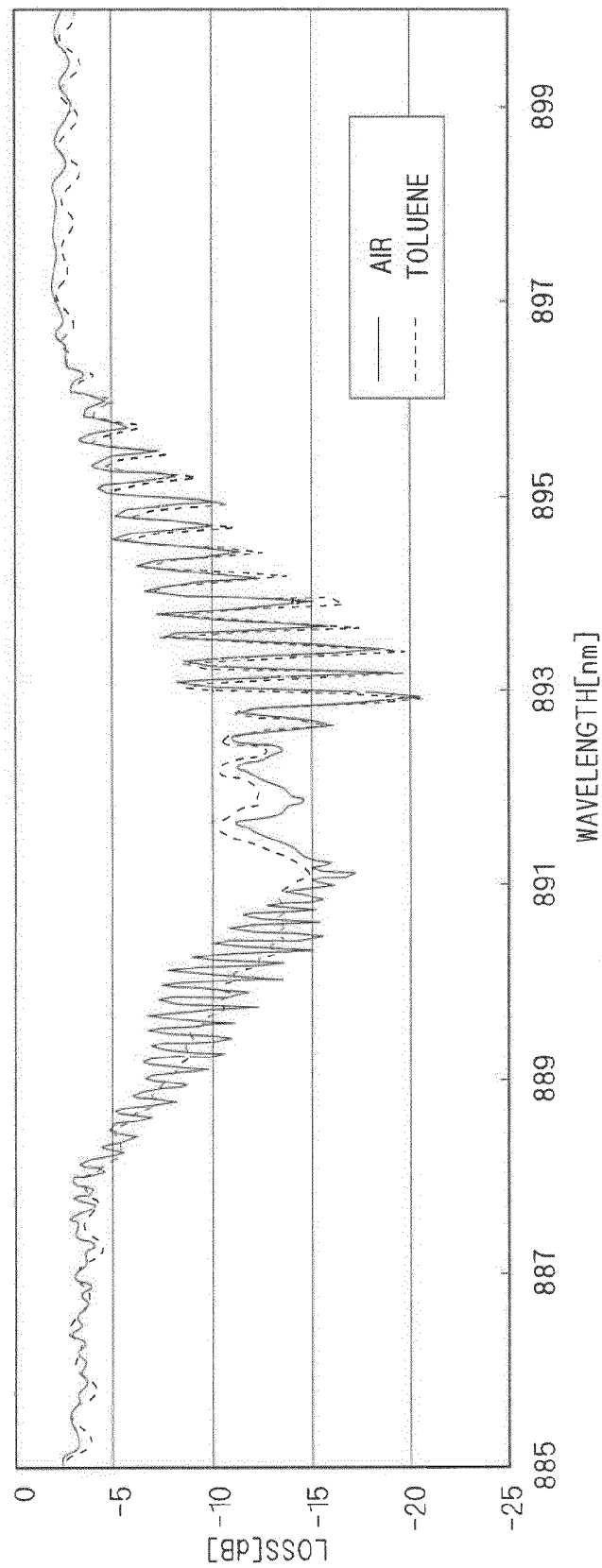
FIG. 18 is a graph showing a transmitted light spectra obtained from the optical fiber sensor according to the sixth preferred embodiment of the present invention.

Next, FIG. 18 shows a transmitted light spectra of the optical fiber sensor in a case where the tilt angle is 4.4°. In the transmitted light spectra of FIG. 18, when the medium to be measured is air, a core reflection mode changes to the cladding mode and sharp transmission loss peaks appear in a wavelength range from about 0.888 to 0.891 µm. Further, in the transmitted light spectra of FIG. 18, sharp transmission loss peaks appear due to reflection in the core in a wavelength range from about 0.892 to 0.896 µm. Since there is no change in the spectra in the case of toluene, it is obvious that this is the reflection mode in the core.

From the above result, it is found that there is no sharp transmission loss peak of the reflection mode in the core in the case where the tilt angle of the grating 109 is 7.3° but sharp transmission loss peaks appear due to the reflection mode in the core in the case where the tilt angle is 4.4°. Therefore, in the case where the optical fiber 101 is a multimode optical fiber, when the tilt angle of the grating 109 is at least not smaller than 0° and smaller than 4.4°, the core reflection mode arises. Further, since sharp transmission loss peaks due to the reflection mode in the core appear and sharp transmission loss peaks due to the cladding mode also appear when the tilt angle of the grating 109 is 4.4°, the cladding mode arises when the tilt angle is at least not smaller than 4.4°.

In the optical fiber sensor of the sixth preferred embodiment, since the grating 109 having a tilt angle not smaller than 4.4° is provided, even if a multimode optical fiber is used as the optical fiber 101, the cladding mode can be caused. Therefore, in the optical fiber sensor of the sixth preferred embodiment, it is possible to detect the refractive index of the medium to be measured which is in contact with the cladding 105 at a region where the grating 109 is formed, from the change in the received light intensity of the light receiving part 103.

Since the core diameter of the multimode optical fiber is larger than that of a single-mode optical fiber, even if a light emitting diode (LED) having a larger area of light emission and smaller directivity of light emission as compared with a laser diode is used as the light source, it is possible to easily couple the light source to the core 104 of the optical fiber 101. Therefore, in the optical fiber sensor of the sixth preferred embodiment, it is possible to increase the amount of change in the received light intensity with respect to the quantity of detected light and the refractive index change. In general, the core diameter of the single-mode optical fiber is about 10 µm or smaller while the core diameter of the multimode optical fiber is larger than 10 µm and that of 50 µm or 62.5 µm is commonly used. Since the multimode optical fiber having a larger core diameter is used in the sixth preferred embodiment, even if a simple method for optically coupling the light source 102 and the optical fiber 101, in which end surfaces of the light source 102 and the optical fiber 101 are directly made proximate to each other, is used without recourse to normal coupling by lenses, it is possible to obtain light of 1 µW or more which is required to carry out high precision measurement.

Further, in the optical fiber sensor of the sixth preferred embodiment, since the core reflection mode which does not change depending on the refractive index of the medium to be measured which is in contact with the cladding 105 is avoided by giving a tilt angle larger than 5.8°, this eliminates the necessity of considering the overlap between the wavelength of the light emitting diode (LED) used as the light source 102 and that of the core reflection mode and makes it possible to prevent influences of an increase in the quantity of detected light and of reflection returning light on light source properties.

The Seventh Preferred Embodiment

The optical fiber sensor of the sixth preferred embodiment can not allow a sufficient detectable range of refractive index when the core diameter of the used optical fiber 101 becomes lager. Then, in the optical fiber sensor of the seventh preferred embodiment, a plurality of gratings 109 having tilt angles are provided, to enlarge a detectable range of refractive index.

In the transmitted light spectra due to the cladding mode in the grating 109, its wavelength range where a loss peak appears depends on the tilt angle and the ratio between the Bragg wavelength and the core diameter. In the grating 109 having a single tilt angle, as the core diameter becomes larger, the upper limit wavelength in the wavelength range of the cladding mode decreases and the lower limit wavelength increases as compared with the case where the core diameter is small. In accordance with the refractive index of the medium to be measured surrounding the cladding 105, the spectra shape of the cladding mode continuously changes and transmitted light intensity changes in a range not larger than the wavelength corresponding to an effective refractive index of the cladding mode. Therefore, the wavelength range of the cladding mode corresponds to the measurement range of refractive index.

Figure 19:
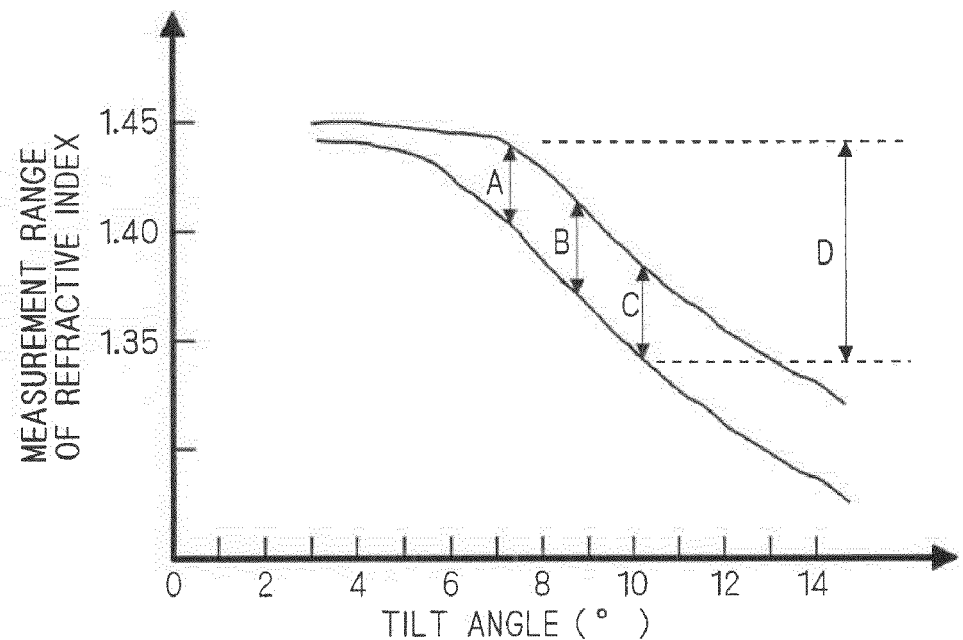
FIG. 19 is an illustration diagram showing a relation between the tilt angle of a grating and the measurement range of refractive index in the optical fiber sensor according to the seventh preferred embodiment of the present invention.

This measurement range of refractive index tends to narrow conversely when the core diameter is made larger in order to obtain a large quantity of measured light. FIG. 19 schematically shows a relation between the measurement range of refractive index and the tilt angle in a case where the multimode optical fiber having a core diameter of 62.5 µm is used near a wavelength of 880 nm. FIG. 19 shows the upper limit and the lower limit of the measurement range of refractive index with respect to the tilt angle, and since the range moves toward the low refractive index side in the order of A, B and C as the tilt angle becomes larger, it is impossible to measure the refractive indices on the low refractive index side and high refractive index side at the same time only by the single grating 109.

Figure 20:
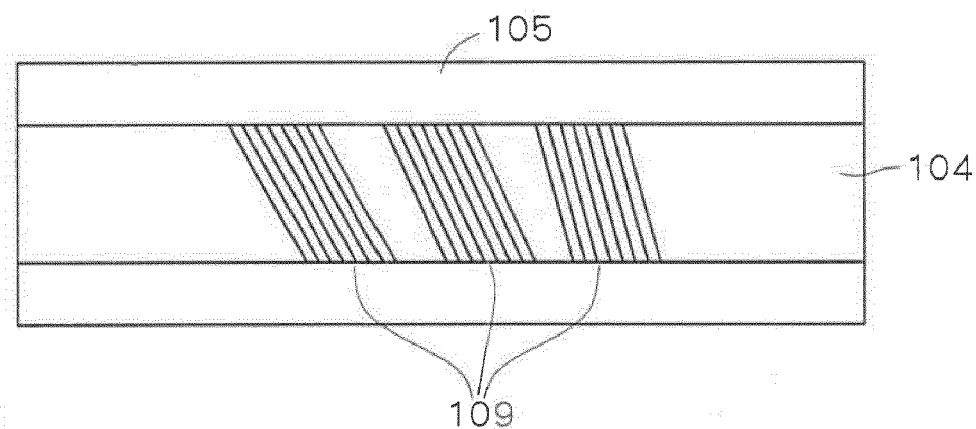
FIG. 20 is a schematic diagram showing the gratings of the optical fiber sensor according to the seventh preferred embodiment of the present invention.
Figure 21:
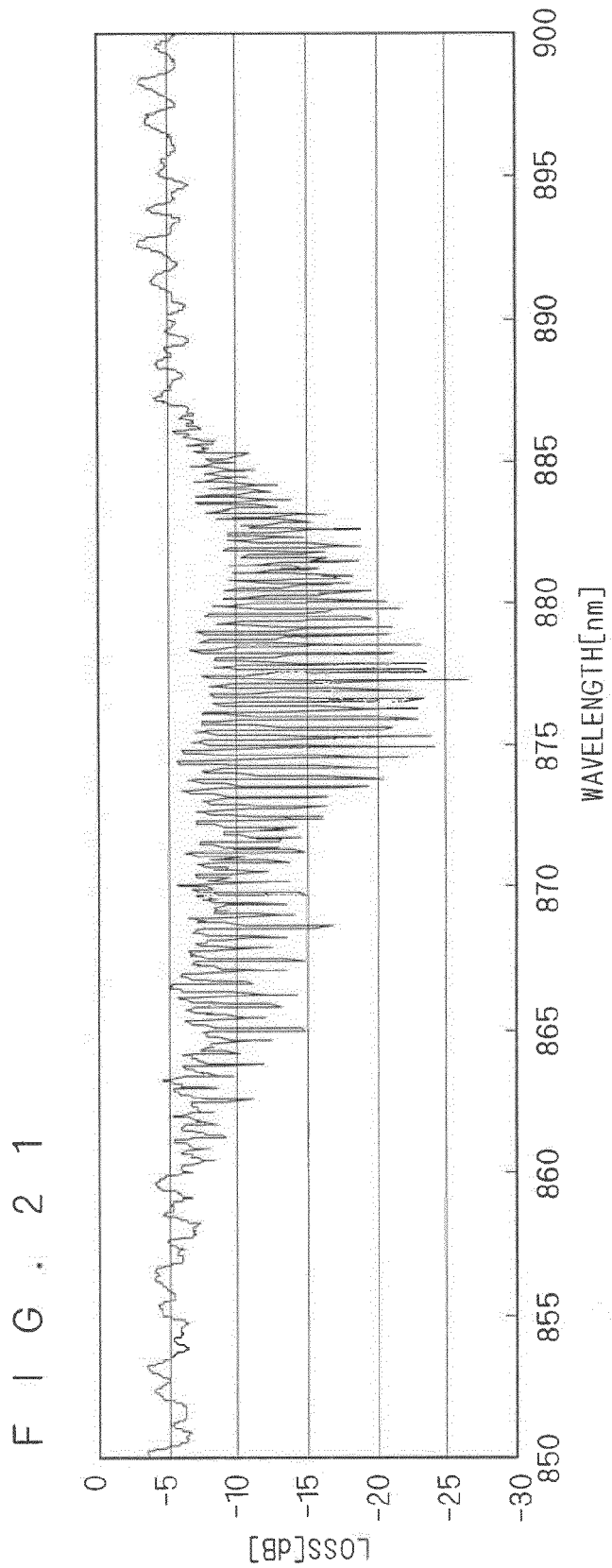
FIG. 21 is a graph showing a transmitted light spectra obtained from the optical fiber sensor according to the seventh preferred embodiment of the present invention.

Then, as the grating 109 of the seventh preferred embodiment, gratings 109 shown in FIG. 20 are adopted. FIG. 20 is a schematic diagram showing an optical fiber in which a plurality of gratings 109 having different tilt angles are formed at different regions of the core 104. In these gratings 109, due to respective cladding modes obtained from the gratings 109 having different tilt angles, transmitted light spectra as shown in e.g. FIG. 21 are observed, being superimposed. Therefore, it is found that the measurement range of refractive index which is a wavelength band where the cladding modes appear is enlarged in the case of using the gratings 109 having different tilt angles as compared with the case of using a grating 109 having a single tilt angle. As can be seen also from the schematic view of FIG. 19, the gratings 109 having different tilt angles have the measurement ranges A, B and C of different refractive indices, respectively, and by forming the gratings 109 as shown in FIG. 20, the measurement range is enlarged like a measurement range D of refractive index.

In the optical fiber sensor of the seventh preferred embodiment, a multimode optical fiber having a cladding diameter of 125 μm and a core diameter of 62.5 μm is used as the optical fiber 101 and the length of each grating 109 is 10 mm. In forming the gratings 109 in the core 104, the multimode optical fiber is irradiated with an ultraviolet laser beam through a phase mask. By controlling the angle of tilt of the phase mask, gratings 109 having arbitrary tilt angles can be formed. Further, the phase mask which is formed so that a plurality of gratings 109 can be formed by single exposure may be used. The tilt angle of the grating refers to an actual tilt angle of a part where the refractive index is changed by exposure in the core. This tilt angle is sometimes different from an angle between the phase mask pattern and the optical fiber because of the refraction effect on a fiber surface. For this reason, in order to form the grating having a desired tilt angle, exposure is performed by using an angle whose value is corrected in advance, which is different from the tilt angle of the grating, as the angle between the phase mask pattern and the optical fiber. The degree of correction depends on the refractive index of a fiber material and the refractive index of the medium surrounding the optical fiber, and if exposure is performed on a quartz-based glass fiber in the air, for example, a value obtained by multiplying a desired tilt angle of the grating by about 0.69 has only to be adopted as the angle between the phase mask pattern and the optical fiber.

The transmitted light spectra shown in FIG. 21 is one obtained in a case where the first grating 109 is formed to have a tilt angle of 7.3°, the next grating 109 is formed to have a tilt angle of 8.8° at a different region and the last grating 109 is formed to have a tilt angle of 10.2° at a further different region. In the transmitted light spectra of FIG. 21, the cladding mode appears in a wide range of 25 nm from 865 to 890 nm and so the measurement range of refractive index can be enlarged as compared with the case of forming only one grating 109. The respective measurement ranges of refractive index for the gratings 109 having different tilt angles are coupled to one another, and a construction can be achieved where the cladding mode continuously changes with respect to the refractive index of the medium to be measured over a wide measurement range of refractive index.

Figure 22:
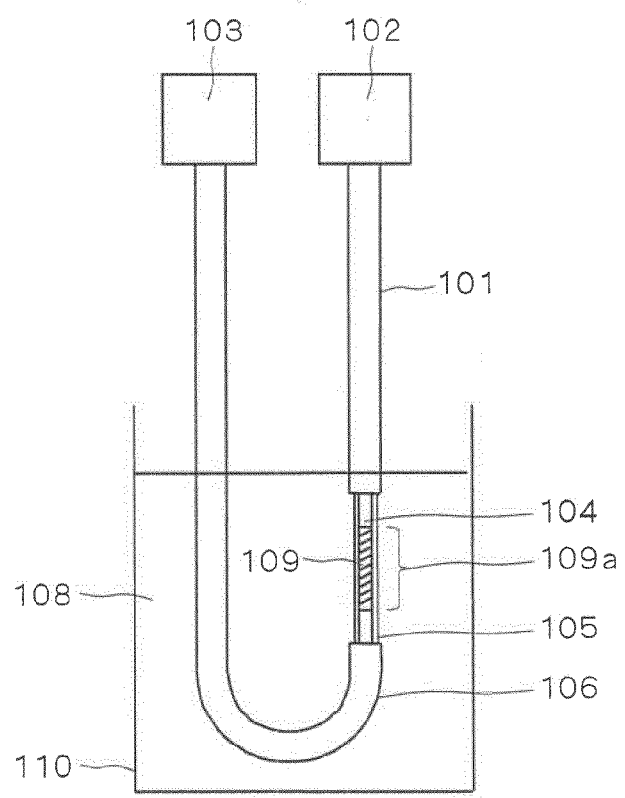
FIG. 22 is a schematic diagram showing the optical fiber sensor according to the seventh preferred embodiment of the present invention.

By using a plurality of gratings 109 having the transmitted light spectra shown in FIG. 21, an optical fiber sensor for detecting a refractive index of liquid, as shown in FIG. 22, is constructed. In the optical fiber sensor of FIG. 22, at an end of the optical fiber 101, the light source 102 is arranged and at the other end thereof, the light receiving part 103 is arranged. The optical fiber 101 comprises the core 104 propagating light emitted from the light source 102, the cladding 105 which is so provided as to cover the core 104 so that the light may be enclosed in the core 104 and the fiber jacket 106 covering and protecting these parts. Further, in the optical fiber 101, for measurement of the refractive index of liquid, part of the fiber jacket 106 is removed so that the cladding 105 may come into direct contact with the liquid 108. In the core 104 at a portion where part of the fiber jacket 106 is removed, a plurality of gratings 109 (hereinafter, sometimes referred to as "multiple tilted-gratings 109a") are formed at different regions, respectively.

As the light source 102, for example, a light emitting diode, a super luminescent diode and the like can be used, and as the light receiving part 103, a light receiving element such as a photodiode and the like can be used to detect the received light intensity. As the core 104 and the cladding 105, inorganic glass such as quartz glass and the like or a plastic-based material such as polymethyl methacrylate and the like can be used. As the fiber jacket 106, a fluorine-based, nylon-based, phenol-based, epoxy-based or melanin-based resin and the like can be used.

Figure 23:
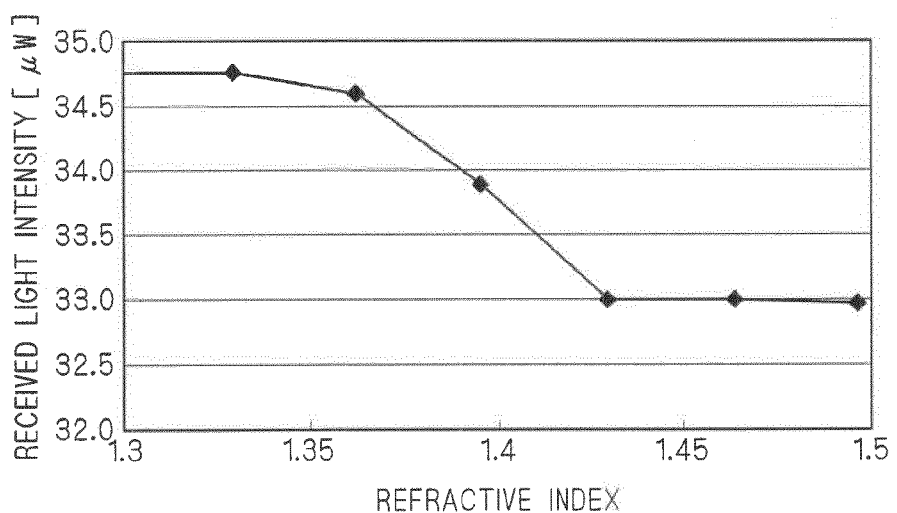
FIG. 23 is the graph showing a relation between a refractive index and the received light intensity obtained from the optical fiber sensor according to the seventh preferred embodiment of the present invention.

FIG. 23 shows the received light intensity with respect to a refractive index of liquid in the optical fiber sensor of the seventh preferred embodiment. In the graph of FIG. 23, the refractive index of liquid is adjusted by changing the mixing ratio between methanol (n=1.329) and toluene (n=1.497). As shown in the graph of FIG. 23, the received light intensity changes dependently on the refractive index of liquid. Therefore, the optical fiber sensor shown in FIG. 22 can detect the refractive index of liquid by reading out the received light intensity by the light receiving part 103.

Though three gratings 109 having the tilt angles of 7.3°, 8.8° and 10.2° are used in the optical fiber sensor of the seventh preferred embodiment, the present invention is not limited to this, but with another grating 109 having a tilt angle of 11.7°, four gratings 109 may be used or with still another grating 109 having a tilt angle of 13.1°, five gratings 109 may be used. Further, in the optical fiber sensor of the seventh preferred embodiment, the used tilt angles are not limited to 7.3°, 8.8° and 10.2° but other angles may be used.

If the optical fiber 101 has a small core diameter, it is possible that the interval of tilt angles is increased and the number of tilt angles to be used is reduced. Conversely, if the optical fiber 101 has a large core diameter, the interval of tilt angles is reduced and the number of tilt angles to be used is increased, to thereby obtain the same transmitted light spectra of the cladding mode. Further, in the case of using a large core diameter, it becomes possible to increase the quantity of light detected by the light receiving part 103 even if a low-intensity light source such as a light emitting diode or the like is used. Furthermore, though the gratings 109 have the tilt angles of +7.3°, +8.8° and +10.2° in the optical fiber sensor of the seventh preferred embodiment, tilt angles with opposite signs, such as +7.3°, −8.8° and +10.2° can be mixed, to have the same effect. The signs (+, −) of the tilt angle refer to the orientation of the grating 109, and if all the tilt angles have the same sign, the gratings 109 have the same orientation as shown in FIG. 20. The order of the gratings 109 having different tilt angles in the optical fiber 101 is not particularly restricted and may not be an ascending order of tilt angles as above.

In the spectra of the used light source 102 such as the light emitting diode or the like, usually, the light intensity varies depending on the wavelength. In order for the optical fiber sensor of the seventh preferred embodiment as a refractive index sensor to improve the linearity of change in output with respect to the refractive index, the intensity of cladding mode in the light source's wavelength range with weak light intensity has only to be compensated. This compensation can be carried out by controlling the lengths of the gratings 109 having different tilt angles or the exposure intensity.

Next, discussion will be made on the pitch of the gratings 109. The measurement range of refractive index for each of the gratings 109 having various tilt angles depends on its tilt angle, not depending on its pitch. For this reason, as to the measurement range of refractive index, the pitch of each grating 109 can be selected arbitrarily. Since the pitch of the grating 109 is in proportion to the appearance wavelength of the cladding mode, however, it is possible to adjust the appearance wavelength of the cladding mode for each grating 109.

In the optical fiber sensor of the seventh preferred embodiment, since exposure is carried out with the pitch of the same phase mask, the appearance wavelength of the cladding mode appears on the short wavelength side in the order of the magnitudes of the tilt angles. Therefore, the wavelength range of the cladding mode in the whole of the gratings 109 depends on the range of tilt angles. It is desirable that the wavelength range of the used light source 102 should be almost equal to the wavelength range of the above cladding mode. For this reason, if the wavelength range of the light source is narrower than that of the cladding mode, the pitch of the grating 109 having the tilt angle corresponding to the short wavelength side of the wavelength range of the cladding mode is increased and the pitch of the grating 109 having the tilt angle corresponding to the long wavelength side is decreased. This allows reduction in the wavelength range of the cladding mode in the whole of the gratings 109 and makes it possible to adjust the wavelength range of the cladding mode to be almost equal to the wavelength range of the light source 102. Therefore, even if the light source 102 having a narrow wavelength range is used, it is possible to improve the linearity with respect to the measured refractive index of the transmitted light intensity.

Thus, in the optical fiber sensor of the seventh preferred embodiment, by forming a plurality of gratings 109 having different tilt angles at different regions, it is possible to enlarge the wavelength range of the cladding mode and detect the refractive index of the liquid which is the medium to be measured in a wide range. Further, in the optical fiber sensor of the seventh preferred embodiment, since an optical fiber having a large core diameter can be used, it is possible to more easily to increase the quantity of light detected by the light receiving part 103.

The Eighth Preferred Embodiment

In an optical fiber sensor of the eighth preferred embodiment, a multimode optical fiber is used as the optical fiber 101 and at one region thereof, a plurality of gratings 109 having different tilt angles are multiply formed.

The optical fiber sensor of the eighth preferred embodiment has almost the same construction as shown in FIG. 22, a multimode optical fiber having a cladding diameter of 125 μm and a core diameter of 62.5 μm is used as the optical fiber 101 and a multiple tilted-grating 109a having a length of 10 mm is formed. In the multiple tilted-grating 109a of the eighth preferred embodiment, however, unlike the multiple tilted-grating 109a shown in FIG. 22, a plurality of gratings 109 having different tilt angles are multiply formed at one region of the core 104 at the region where part of the fiber jacket 106 is removed. In forming the gratings 109, the multimode optical fiber is irradiated with an ultraviolet laser beam through a phase mask. Then, by controlling the angle of tilt of the phase mask, gratings 109 having arbitrary tilt angles can be formed.

In the multiple tilted-grating 109a of the eighth preferred embodiment, as shown in FIG. 24, the grating 109 having a tilt angle of 7.3° is first formed, the grating 109 having a tilt angle of 8.8° is subsequently formed and the grating 109 having a tilt angle of 10.2° is finally formed. FIG. 25 shows a transmitted light spectra of the manufactured multiple tilted-grating 109a. In the transmitted light spectra of FIG. 25, the cladding mode appears in a wide range of 25 nm from 865 to 890 nm. Though the gratings 109 having different tilt angles are formed at different regions, respectively, in the multiple tilted-grating 109a of the seventh preferred embodiment, the gratings 109 having different tilt angles are multiply formed at one region in the multiple tilted-grating 109a of the eighth preferred embodiment. Also in the case of the multiple tilted-grating 109a of the eighth preferred embodiment, like the multiple tilted-grating 109a of the seventh preferred embodiment, the wavelength range of the cladding mode can be enlarged as compared with the optical fiber sensor with only one grating 109 formed.

Figure 26:
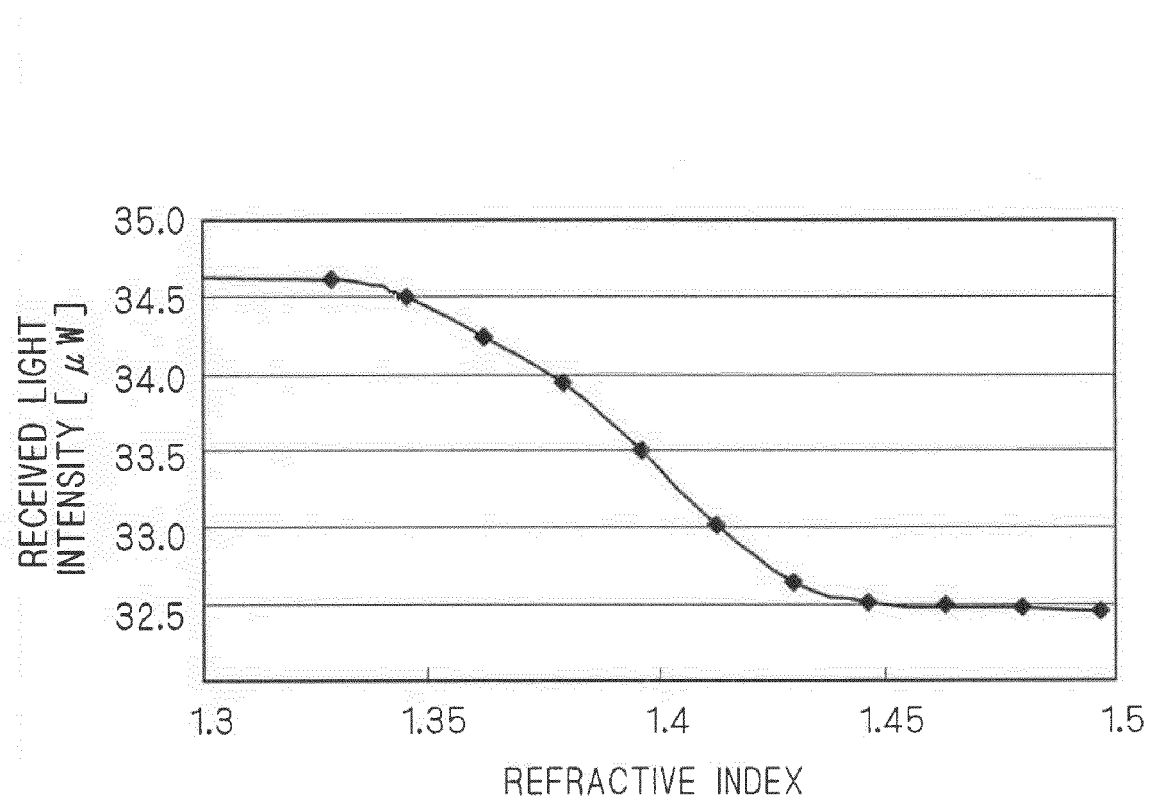
FIG. 26 is a graph showing a relation between a refractive index and the received light intensity obtained from the optical fiber sensor in accordance with the eighth preferred embodiment of the present invention.

FIG. 26 shows a result of measurement of the received light intensity with respect to the refractive index of the liquid which is the medium to be measured, performed by using the optical fiber sensor of the eighth preferred embodiment. The refractive index of liquid is adjusted by changing the mixing ratio between methanol (n=1.329) and toluene (n=1.497). In the graph of FIG. 26, like in the graph of FIG. 23 discussed in the seventh preferred embodiment, the received light intensity changes dependently on the refractive index of liquid. Therefore, the optical fiber sensor of the eighth preferred embodiment can also detect the refractive index of the liquid which is the medium to be measured by reading out the received light intensity.

Thus, in the optical fiber sensor of the eighth preferred embodiment, since a plurality of gratings 109 having different tilt angles are multiply formed at one region, it is possible to enlarge the wavelength range of the cladding mode and detect the refractive index of the liquid which is the medium to be measured, like in the case where a plurality of gratings 109 having different tilt angles are formed at different regions. Further, in the optical fiber sensor of the eighth preferred embodiment, since a plurality of gratings 109 having different tilt angles are multiply formed at one region, it is possible to reduce the size of a region where the gratings 109 serving as a sensor part are formed.

While the invention has been shown and described in detail, the foregoing description is in all aspects illustrative and not restrictive. It is therefore understood that numerous modifications and variations can be devised without departing from the scope of the invention.

The invention claimed is:

1. An optical fiber sensor comprising:
   an optical fiber comprising a core with a Bragg grating formed therein and a cladding, in which a transmission loss is caused by a leakage in a cladding propagation mode at a portion of the cladding at a position where the Bragg grating is formed;
   a light source for emitting light of the wavelength band in the cladding propagation mode into the optical fiber; and
   a light receiving part for receiving a transmitted light or a reflected light of the light passing through the core and the cladding at a position where the Bragg grating is formed, the light receiving part receiving transmitted or reflected light that passes through an end of the core and cladding and does not pass through an outer side of the cladding into a surrounding media, the sensor determining an index of refraction of the surrounding media based on an intensity of total light received by the light receiving part,
   wherein the Bragg grating comprises a plurality of Bragg gratings having different tilt angles with respect to a vertical line in a longitudinal direction of the optical fiber, and the plurality of Bragg gratings have the respective tilt angles that are adjusted so that detectable ranges of refractive indices of the surrounding media to be measured partially overlap, and the surrounding media to be measured is in contact with the cladding.

2. The optical fiber sensor according to claim 1, wherein the plurality of Bragg gratings having the different tilt angles are formed at a plurality of regions, respectively.

3. The optical fiber sensor according to claim 1, wherein the plurality of Bragg gratings having the different tilt angles are formed at one region.

* * * * *